(12) United States Patent
Reiley et al.

(10) Patent No.: US 6,899,719 B2
(45) Date of Patent: May 31, 2005

(54) SYSTEMS AND METHODS FOR TREATING FRACTURED OR DISEASED BONE USING EXPANDABLE BODIES

(75) Inventors: Mark A Reiley, Piedmont, CA (US); Arie Scholten, Fremont, CA (US); Karen D Talmadge, Palo Alto, CA (US); Robert M Scribner, Los Altos, CA (US)

(73) Assignee: Kyphon Inc., Sunnyvale, CA (US)

( * ) Notice: Subject to any disclaimer, the term of this patent is extended or adjusted under 35 U.S.C. 154(b) by 448 days.

(21) Appl. No.: 09/754,451

(22) Filed: Jan. 4, 2001

(65) Prior Publication Data

US 2001/0049531 A1 Dec. 6, 2001

Related U.S. Application Data

(63) Continuation of application No. 08/871,114, filed on Jun. 9, 1997, now Pat. No. 6,248,110, which is a continuation-in-part of application No. 08/659,678, filed on Jun. 5, 1996, now Pat. No. 5,827,289, which is a continuation-in-part of application No. 08/485,394, filed on Jun. 7, 1995, now abandoned, which is a continuation-in-part of application No. 08/188,224, filed on Jan. 26, 1994, now abandoned.

(51) Int. Cl.$^7$ .............................................. A61B 17/56
(52) U.S. Cl. ...................... 606/192; 606/61; 604/96.01; 600/207
(58) Field of Search ....................... 623/17.12; 606/92, 606/93, 94, 192, 193, 194; 600/207; 604/96.01

(56) References Cited

U.S. PATENT DOCUMENTS

| | | |
|---|---|---|
| 1,965,653 A | 7/1934 | Kennedy |
| 3,091,237 A | 5/1963 | Skinner |
| 3,112,743 A | 12/1963 | Cochran et al. |
| 3,626,949 A | 12/1971 | Shute |
| 3,648,294 A | 3/1972 | Shahrestani |
| 3,800,788 A | 4/1974 | White |

(Continued)

FOREIGN PATENT DOCUMENTS

| | | |
|---|---|---|
| FR | 439636 | 5/1912 |
| GB | 512456 | 9/1939 |
| NL | 9001858 | 3/1992 |
| RU | 906530 | 2/1982 |
| RU | 1148610 | 4/1985 |
| WO | WO 97/28840 | 8/1997 |
| WO | WO 98/56301 | 12/1998 |
| WO | WO 99/02214 | 1/1999 |
| WO | WO 99/37212 | 7/1999 |
| WO | WO 99/62416 | 12/1999 |
| WO | WO 00/09024 | 2/2000 |
| WO | WO 01/76492 | 10/2001 |
| WO | WO 01/76514 | 10/2001 |

OTHER PUBLICATIONS

Urist, Marshal R., "Closed Intramedullary Rodding of Pathologic Fractures with Supplemental Cement", Clinical Orthopaedics and Related Research, No. 188, pp. 183–186; 1984.

(Continued)

*Primary Examiner*—Julian W. Woo
(74) *Attorney, Agent, or Firm*—Ryan Kromholz & Manion, SC

(57) ABSTRACT

Systems and methods treat fractured or diseased bone by deploying more than a single therapeutic tool into the bone. In one arrangement, the systems and methods deploy an expandable body in association with a bone cement nozzle into the bone, such that both occupy the bone interior at the same time. In another arrangement, the systems and methods deploy multiple expandable bodies, which occupy the bone interior volume simultaneously. Expansion of the bodies form cavity or cavities in cancellous bone in the interior bone volume.

34 Claims, 31 Drawing Sheets

U.S. PATENT DOCUMENTS

| | | |
|---|---|---|
| 3,875,595 A | 4/1975 | Kroning |
| 3,889,665 A | 6/1975 | Ling et al. |
| 3,997,138 A | 12/1976 | Crock et al. |
| 4,205,683 A | 6/1980 | O'Neill |
| 4,274,163 A | 6/1981 | Malcom et al. |
| 4,313,434 A | 2/1982 | Segal |
| 4,369,772 A | 1/1983 | Miller |
| 4,399,814 A | 8/1983 | Pratt, Jr. et al. |
| 4,432,358 A | 2/1984 | Fixel |
| 4,462,394 A | 7/1984 | Jacobs |
| 4,466,435 A | 8/1984 | Murray |
| 4,467,479 A | 8/1984 | Brody |
| 4,488,549 A | 12/1984 | Lee et al. |
| 4,494,535 A | 1/1985 | Haig |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,653,489 A | 3/1987 | Tronzo |
| 4,685,447 A * | 8/1987 | Iversen et al. ........... 604/96.01 |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,772,287 A | 9/1988 | Ray et al. |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,969,888 A * | 11/1990 | Scholten et al. ............... 606/94 |
| 4,987,892 A | 1/1991 | Krag et al. |
| 5,053,035 A | 10/1991 | McLaren |
| 5,071,435 A | 12/1991 | Fuchs et al. |
| 5,100,390 A | 3/1992 | Lubeck et al. |
| 5,102,413 A | 4/1992 | Poddar |
| 5,108,404 A | 4/1992 | Scholten et al. |
| 5,116,305 A | 5/1992 | Milder et al. |
| 5,127,912 A | 7/1992 | Ray et al. |
| 5,147,366 A | 9/1992 | Arroyo et al. |
| 5,163,989 A | 11/1992 | Campbell et al. |
| 5,176,683 A | 1/1993 | Kimsey et al. |
| 5,176,692 A | 1/1993 | Wilk et al. |
| 5,284,473 A * | 2/1994 | Calabria ..................... 606/192 |
| 5,295,962 A * | 3/1994 | Crocker et al. ............. 606/194 |
| 5,303,718 A | 4/1994 | Krajicek |
| 5,330,429 A | 7/1994 | Nogochi et al. |
| 5,331,975 A | 7/1994 | Bonutti |
| 5,359,995 A | 11/1994 | Sewell, Jr. |
| 5,361,752 A | 11/1994 | Moll et al. |
| 5,383,932 A | 1/1995 | Wison et al. |
| 5,397,307 A * | 3/1995 | Goodin .................... 604/96.01 |
| 5,423,850 A | 6/1995 | Berger |
| 5,441,538 A | 8/1995 | Bonutti |
| 5,454,365 A | 10/1995 | Bonutti |
| 5,456,267 A | 10/1995 | Stark |
| 5,467,786 A | 11/1995 | Allen et al. |
| 5,468,245 A | 11/1995 | Vargas, III |
| 5,480,400 A | 1/1996 | Berger |
| 5,514,143 A | 5/1996 | Bonutti et al. |
| 5,514,153 A | 5/1996 | Bonutti |
| 5,522,790 A | 6/1996 | Moll et al. |
| 5,522,846 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,540,711 A | 7/1996 | Kieturakis et al. |
| 5,545,136 A | 8/1996 | Berger |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,601,590 A | 2/1997 | Bonutti et al. |
| 5,674,295 A * | 10/1997 | Ray et al. ................. 623/17.12 |
| 5,788,703 A | 8/1998 | Mittelmeier et al. |
| 5,792,044 A | 8/1998 | Foley et al. |
| 5,817,074 A | 10/1998 | Racz |
| 5,827,289 A | 10/1998 | Reiley et al. |
| 5,849,014 A | 12/1998 | Mastrorio et al. |
| 5,865,728 A | 2/1999 | Moll et al. |
| 5,928,162 A | 7/1999 | Giurtino et al. |
| 5,947,977 A * | 9/1999 | Slepian et al. ............... 606/194 |
| 5,961,499 A | 10/1999 | Bonutti et al. |
| 5,972,015 A | 10/1999 | Scribner et al. |
| 5,976,105 A | 11/1999 | Marcove et al. |
| 6,036,682 A | 3/2000 | Lange et al. |
| 6,036,711 A | 3/2000 | Mozdzierz et al. |
| 6,048,346 A | 4/2000 | Reiley et al. |
| 6,066,154 A | 5/2000 | Reiley et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,440,138 B1 | 8/2002 | Reiley et al. |
| 6,468,279 B1 | 10/2002 | Reo |
| 6,582,446 B1 | 6/2003 | Marchosky |
| 6,607,544 B1 | 8/2003 | Boucher et al. |
| 2002/0010472 A1 | 1/2002 | Kuslich et al. |
| 2002/0032447 A1 | 3/2002 | Weikel et al. |
| 2002/0099385 A1 | 7/2002 | Ralph et al. |
| 2003/0050702 A1 | 3/2003 | Berger |
| 2003/0130664 A1 | 7/2003 | Boucher et al. |

OTHER PUBLICATIONS

B. Lawrence Riggs, M.D. et al., "Medical Progress, Involutional Osteoporosis", The New England Journal of Medicine, Jun. 26, 1986, pp. 1676–1686.

Lawrence D. Cohen, M.D., "Fractures of the Osteoporotic Spine", Pathologic Fractures in Betabolic Bone Disease, The Orthopedic Clinics of North America, vol. 21:1, Jan. 1990, pp. 143–152.

S.L. Silverman, "The Clinical Consequences of Vertebral Compression Fracture", Bone, 13, S27–S31 (1992).

Melton, III, L. Joseph et al., "Perspective: How Many Women Have Osteoporosis", Journal of Bone and Mineral Research, vol. 7, No. 9, 1992, pp. 1005–1010.

Harrington, Kevin D., The Use of Methylmethacrylate as an Adjunct in the Internal Fixation of Malignant Neoplastic Fractures, The Journal of Bone and Joint Surgery, vol. 54A, No. 8, Dec. 1972, pp. 1665–1676.

Instructions entitled "Exeter Pressurizer System", by Howmedica Inc., Orthopaedics Division, 1979, 2 pages.

* cited by examiner

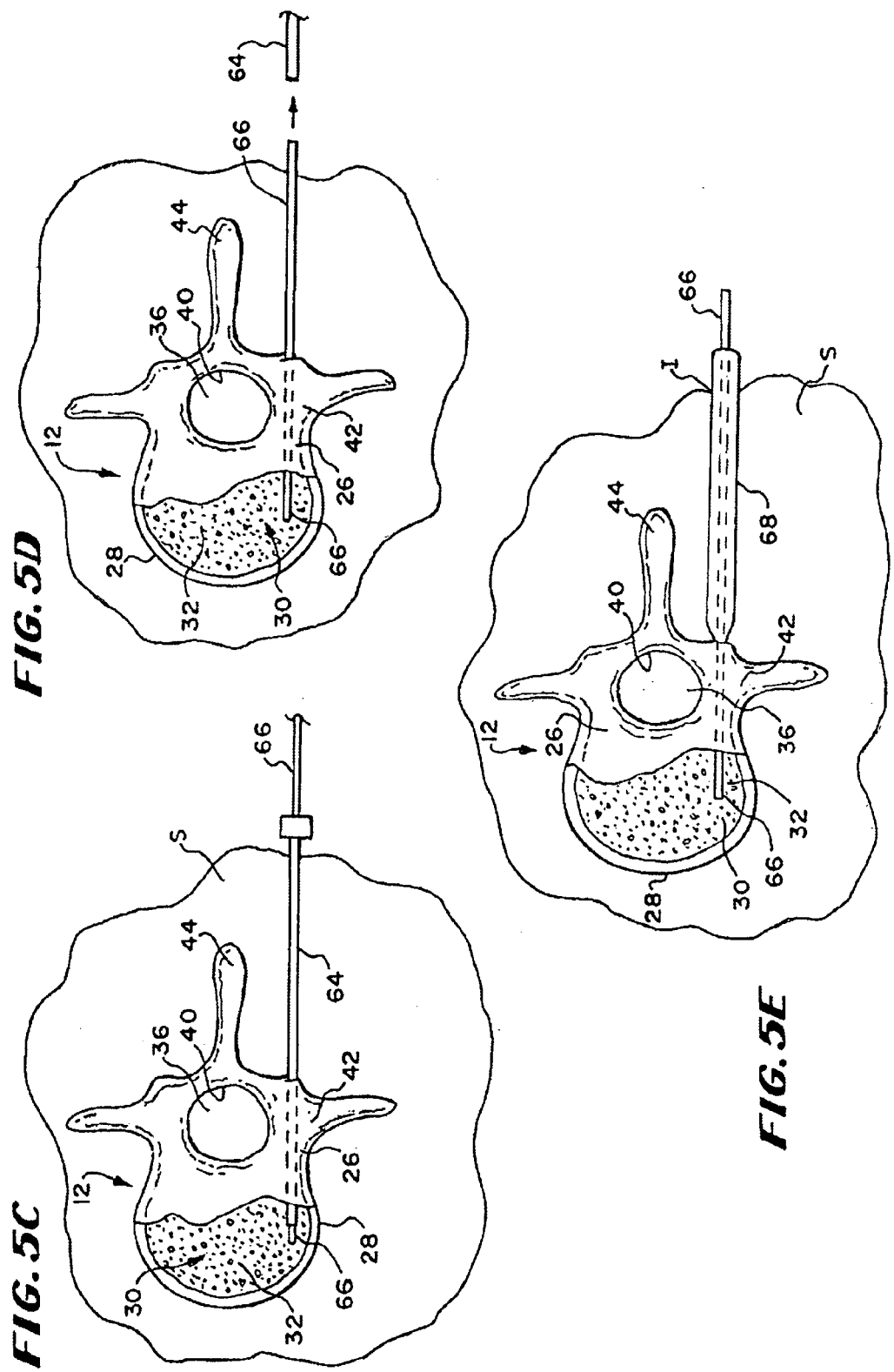

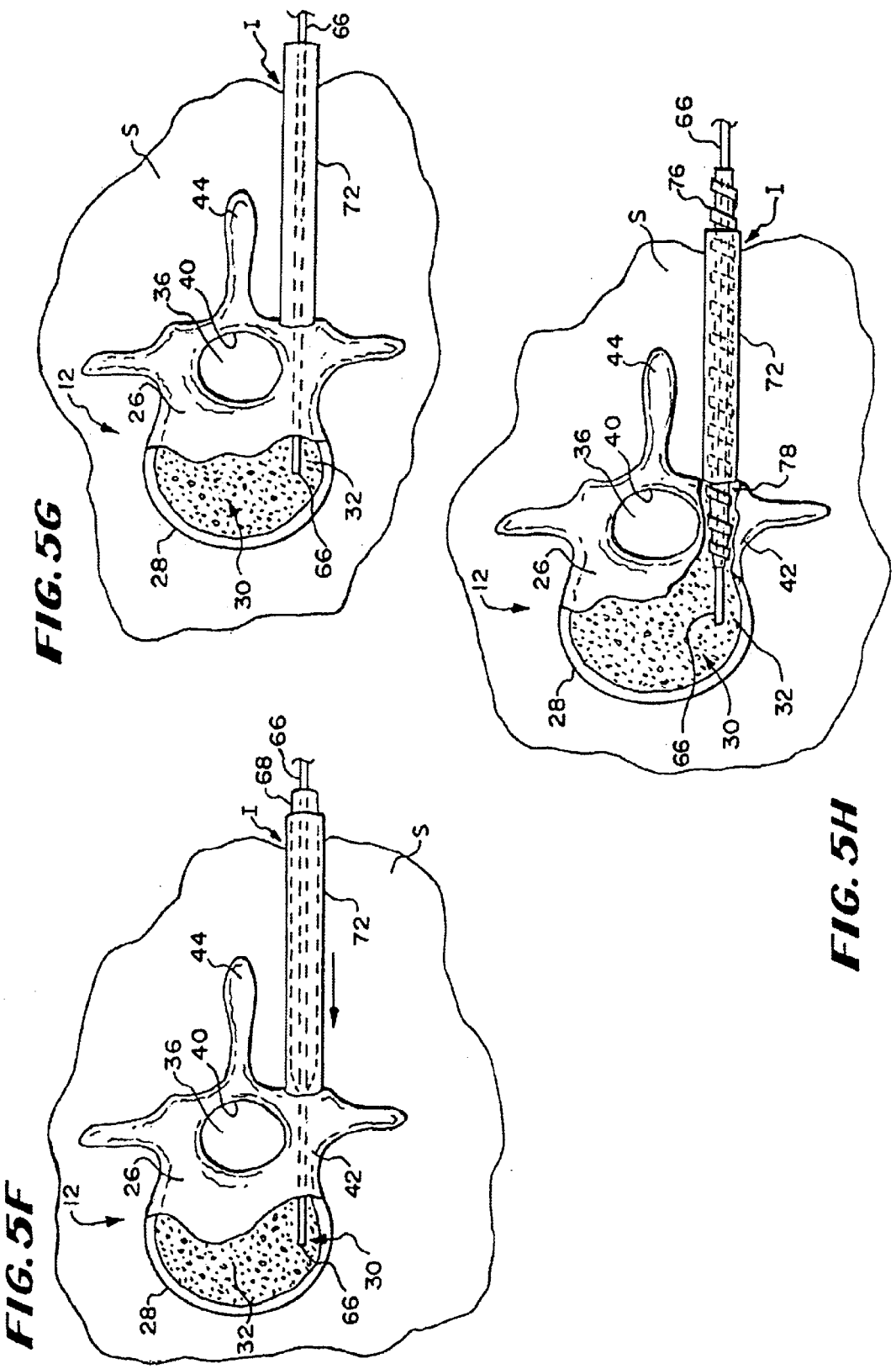

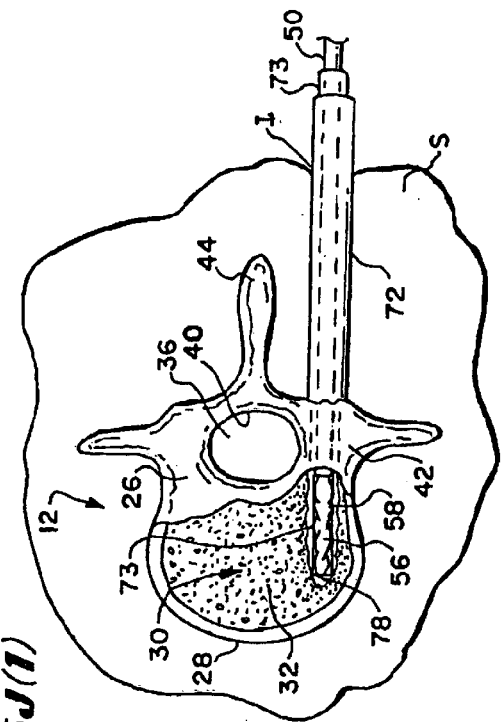
FIG.5I
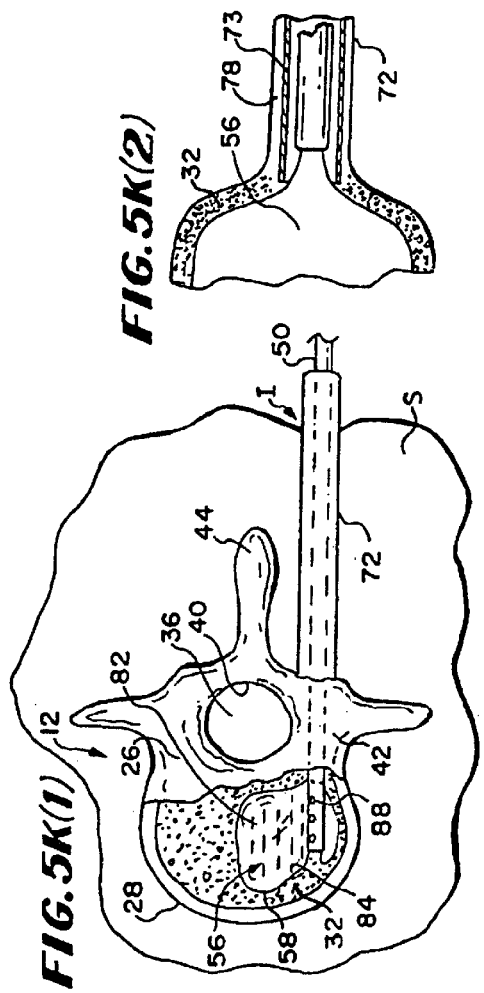
FIG.5J(1)
FIG.5J(2)
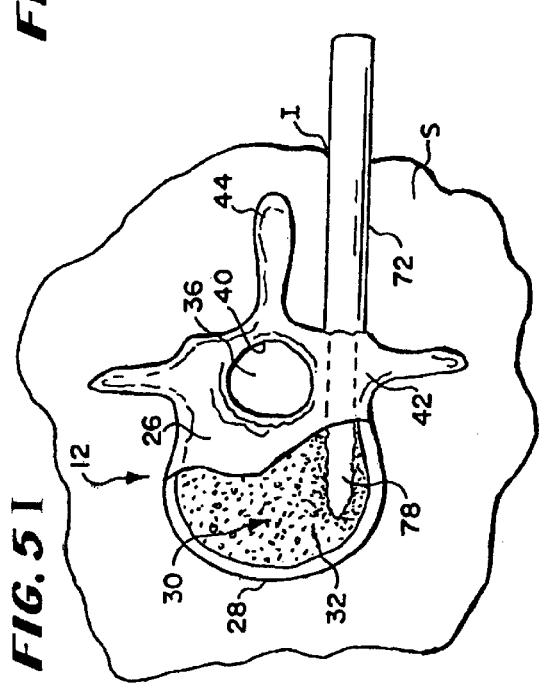
FIG.5K(1)
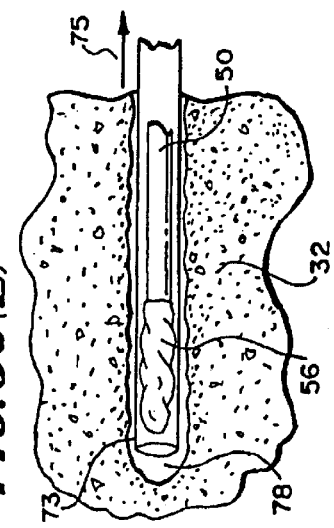
FIG.5K(2)

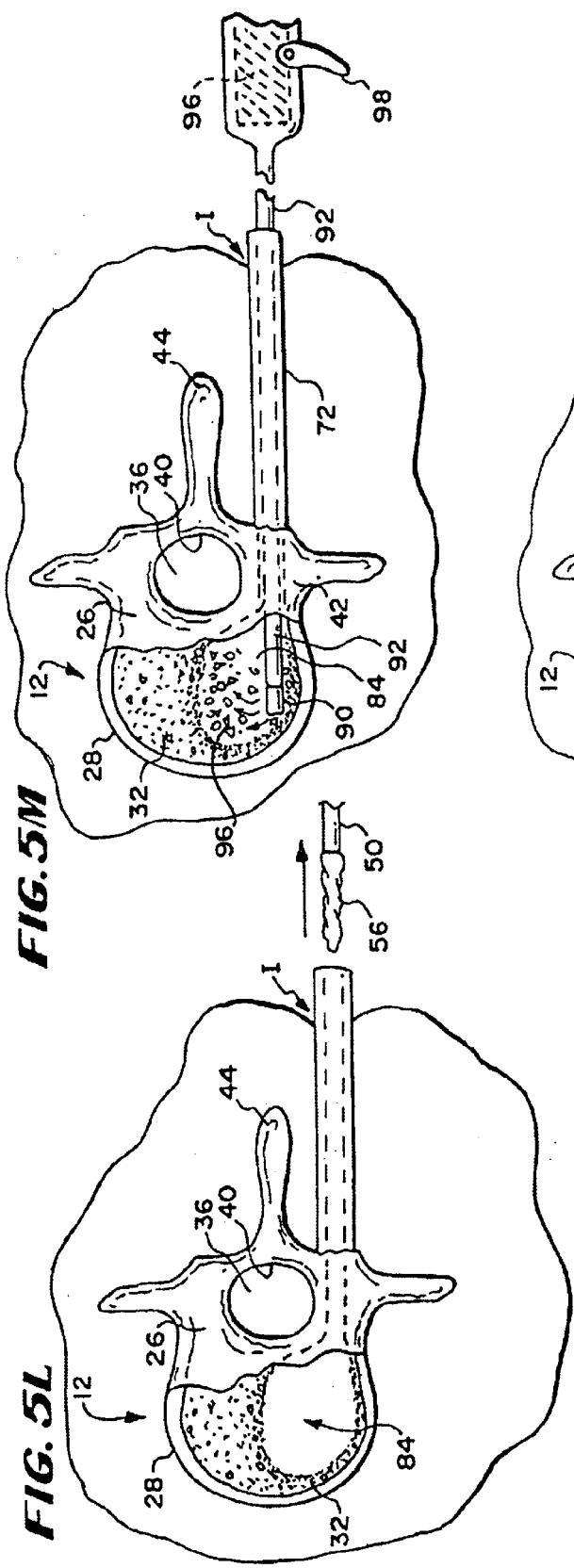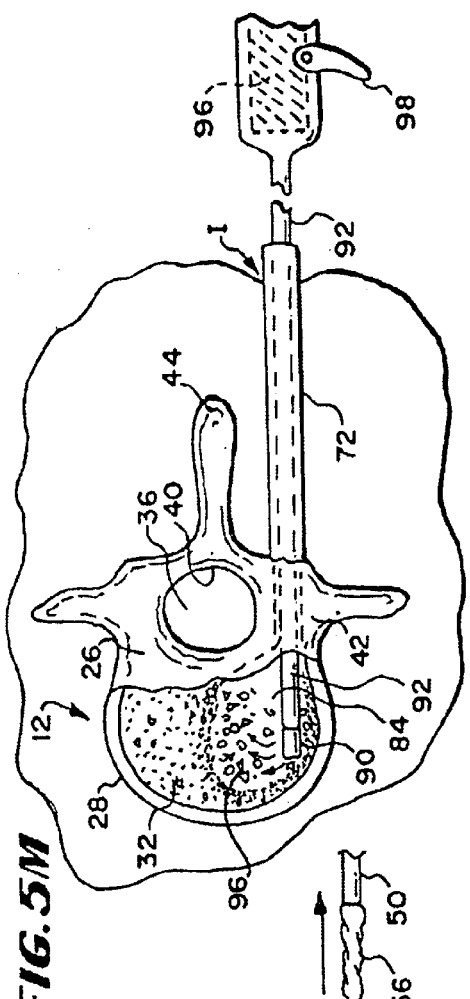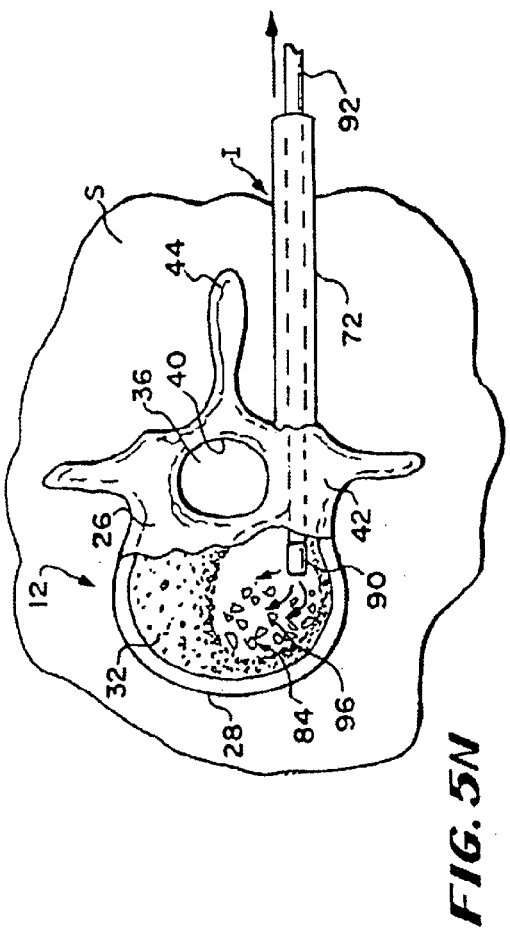

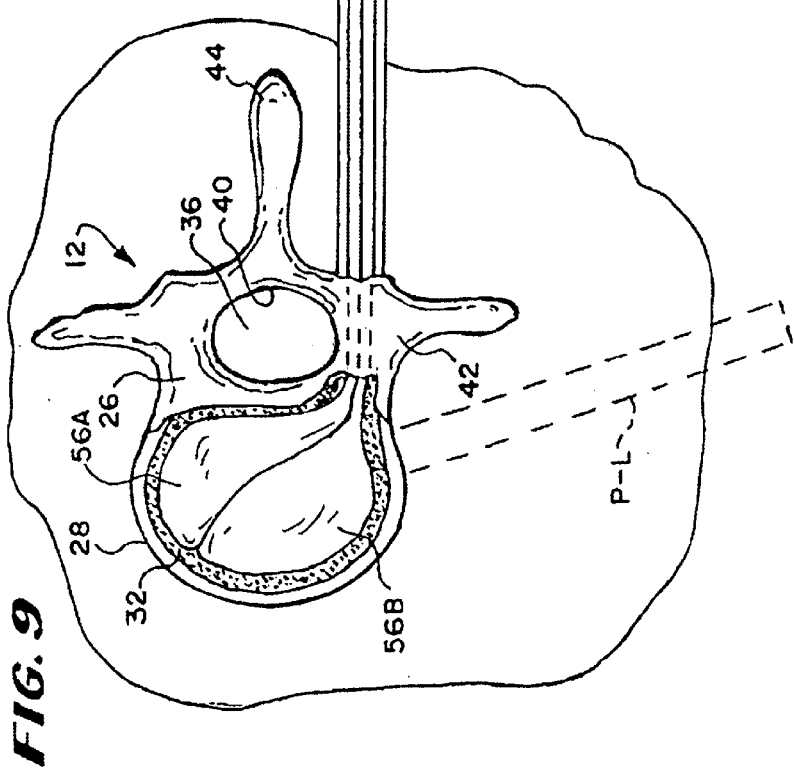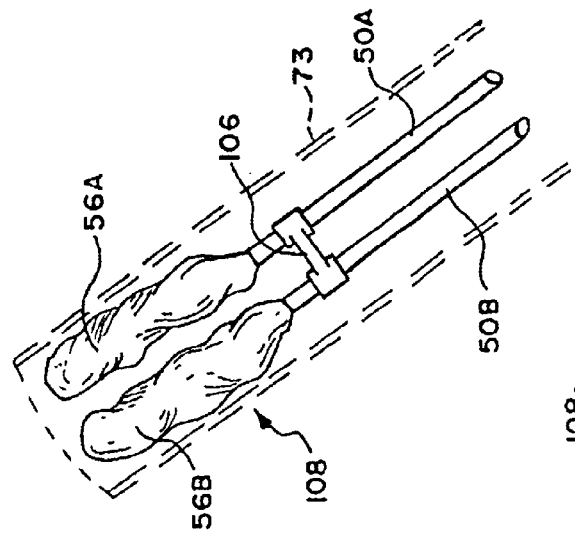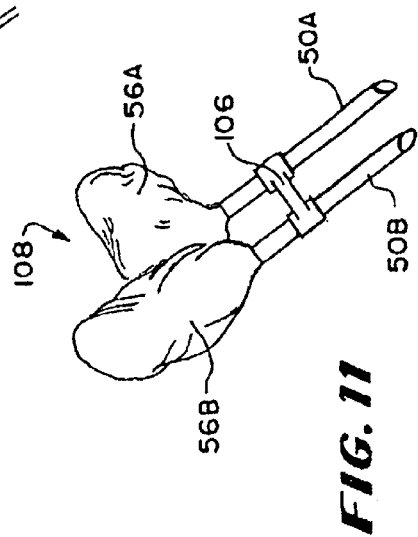

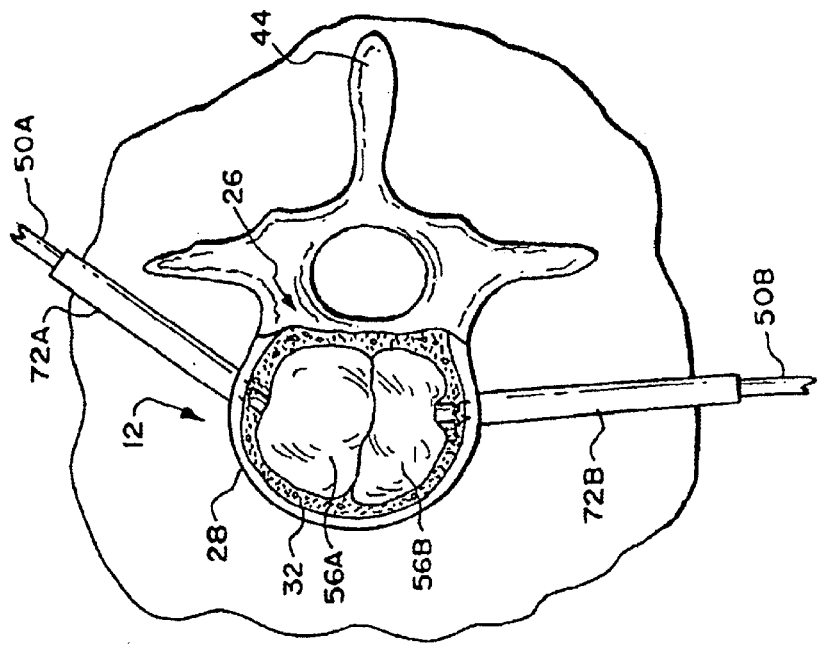
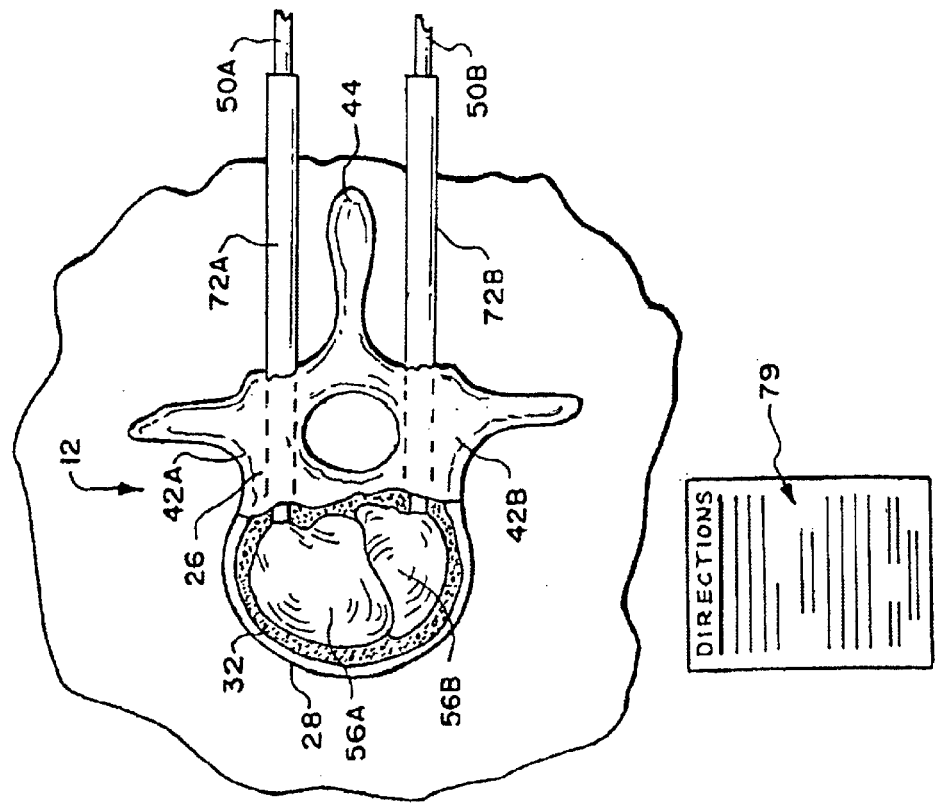

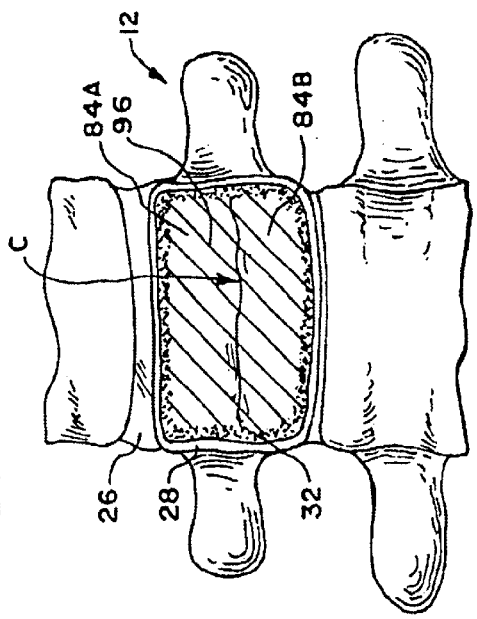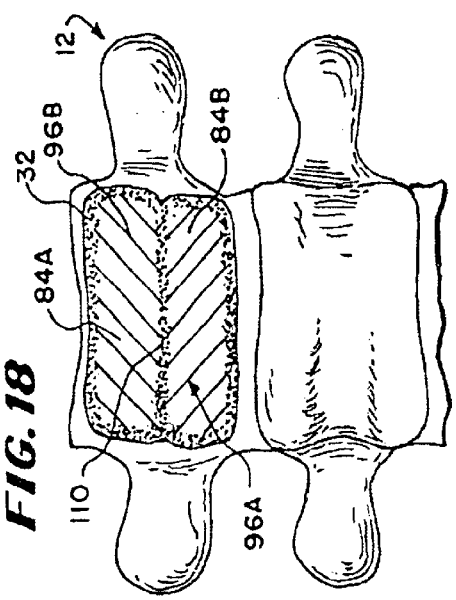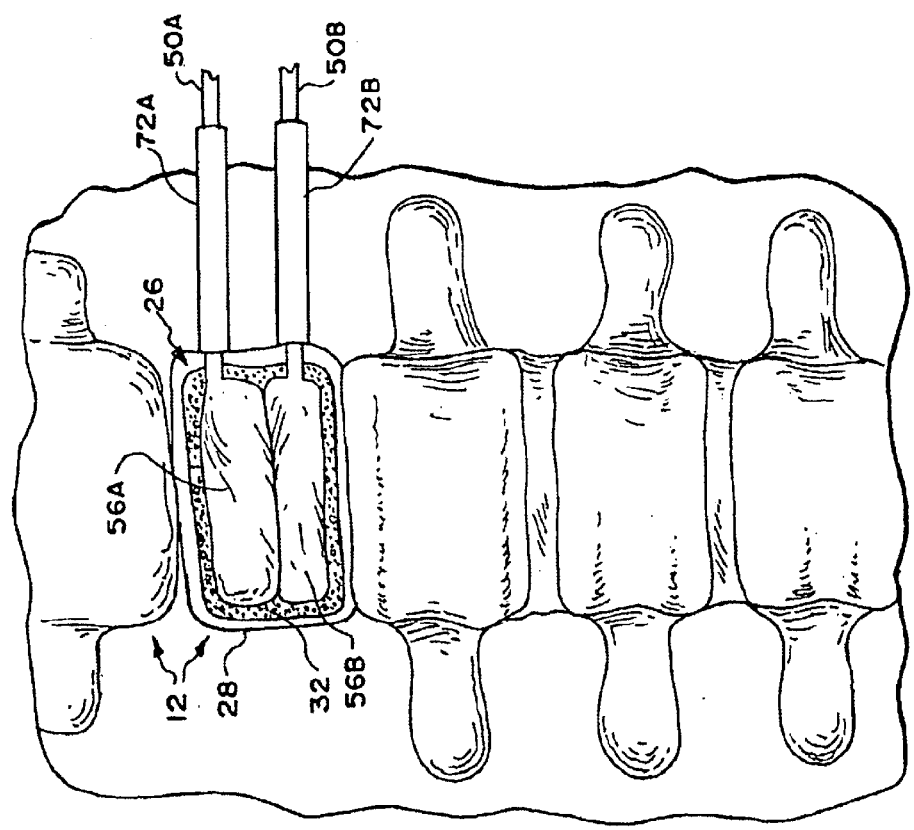

SYSTEMS AND METHODS FOR TREATING FRACTURED OR DISEASED BONE USING EXPANDABLE BODIES

RELATED APPLICATIONS

This application is a continuation of copending application Ser. No. 08/871,114 filed Jun. 9, 1997 now U.S. Pat. No. 6,248,110

This application is a continuation-in-part of U.S. patent application Ser. No. 08/659,678, filed Jun. 5, 1996 now U.S. Pat. No. 5,827,289, which is a continuation-in-part of U.S. patent application Ser. No. 08/485,394, filed Jun. 7, 1995 now abandoned, which is a continuation-in-part of U.S. patent application Ser. No. 08/188,224, filed Jan. 26, 1994 now abandoned, entitled, "Improved Inflatable Device For Use In Surgical Protocol Relating To Fixation Of Bone."

FIELD OF THE INVENTION

The invention relates to the treatment of bone conditions in humans and other animals.

BACKGROUND OF THE INVENTION

When cancellous bone becomes diseased, for example, because of osteoporosis, avascular necrosis, or cancer, the surrounding cortical bone becomes more prone to compression fracture or collapse. This is because the cancellous bone no longer provides interior support for the surrounding cortical bone.

There are 2 million fractures each year in the United States, of which about 1.3 million are caused by osteoporosis alone. There are also other bone disease involving infected bone, poorly healing bone, or bone fractured by severe trauma. These conditions, if not successfully treated, can result in deformities, chronic complications, and an overall adverse impact upon the quality of life.

U.S. Pat. Nos. 4,969,888 and 5,108,404 disclose apparatus and methods for the fixation of fractures or other conditions of human and other animal bone systems, both osteoporotic and non-osteoporotic. The apparatus and methods employ an expandable body to compress cancellous bone and provide an interior cavity. The cavity receives a filling material, which hardens and provides renewed interior structural support for cortical bone.

The better and more efficacious treatment of bone disease that these Patents promise can be more fully realized with improved systems and methods for making and deploying expandable bodies in bone.

SUMMARY OF THE INVENTION

The invention provides improved systems and methods for treating bone, including vertebral bodies, as well as in other bone types, using one or more expandable bodies.

One aspect of the invention provides systems and methods for treating bone using an expandable wall in association with a nozzle for discharging a material. According to this aspect of the invention, the systems and methods insert both the body and the nozzle into a bone having cortical bone surrounding an interior volume occupied, at least in part, by cancellous bone. The systems and methods causing the body to assume an expanded geometry while occupying the interior volume in the presence of the nozzle to compact cancellous bone and form a cavity in the interior volume. The systems and methods convey a material for discharge through the nozzle into the cavity at least partially while the body occupies the interior volume.

In a preferred embodiment, the systems and methods convey bone cement for discharge through the nozzle, while the body is in the expanded geometry or a partially expanded geometry. The systems and methods can also cause the expanded geometry of the body to decrease in volume in relation to volume of material discharged by the nozzle into the cavity.

In one embodiment, the expandable body and nozzle are deployed separately into the targeted bone. In a preferred embodiment, the expandable body and nozzle form a integrated tool and are deployed simultaneously into the targeted bone.

Another aspect of the invention provides systems and methods for treating bone using first and second expandable bodies. The first expandable body is inserted into the interior bone volume through a first access path in cortical bone. The second expandable body is inserted into the same interior bone volume through a second access path in cortical bone different than the first access path. The systems and methods cause each of the bodies to assume an expanded geometry for jointly compacting cancellous bone to form a cavity in the interior volume.

In one embodiment, the first and second access paths comprise different ipsilateral posterolateral accesses. In another embodiment, the first and second access paths comprise different transpedicular accesses. In yet another embodiment, the first a second access paths comprise a transpedicular access and a postereolateral access.

Another aspect of the invention provides a body for insertion into a bone, which comprises two expandable zones. The first zone assumes an elongated expanded geometry. The elongated geometry presents a first dimension, which extends substantially across the interior volume, to form a barrier within the interior volume. The elongated geometry also presents a second dimension less than the first dimension, which leaves a region of substantially uncompacted cancellous bone extending from the barrier within the interior volume. The second expandable zone assumes a different expanded geometry, which compacts cancellous bone to form a cavity in the region. The barrier formed by the first zone directs expansion of the second zone in the region away from the first zone.

In one embodiment, the first and second expandable zones comprise separate expandable assemblies. In another embodiment, the first and second expandable zone comprise parts of a single expandable assembly.

Features and advantages of the inventions are set forth in the following Description and Drawings, as well as in the appended claims.

BRIEF DESCRIPTION OF THE DRAWINGS

FIG. 9 is a coronal view of a vertebral body showing multiple expandable bodies separately introduced by transpedicular approach;

FIG. 10 is a view of the distal end of a probe in which two catheter tubes, each carrying an expandable body, are joined to form a symmetric array, when substantially expanded outside a bone;

FIG. 11 is a view of the distal end of a probe in which two catheter tubes, each carrying an expandable body, are joined to form an asymmetric array, when substantially expanded outside a bone;

FIG. 12 is a coronal view, partially broken away and in section, of a vertebral body into which multiple expandable bodies have been deployed by dual transpedicular access;

FIG. 13 is a coronal view of a vertebral body, partially broken away and in section, into which multiple expandable bodies have been deployed by contralateral posterolateral access;

FIG. 16 is an anterior-posterior view of a region of the spine, showing multiple expandable bodies present within a targeted vertebral body using ipsilateral postereolateral access;

FIG. 17 is an anterior-posterior view of a vertebral body, partially broken away and in section, in which multiple expandable bodies, introduced using ipsilateral postereolateral access, have formed multiple cavities which are joined to form a single cavity to receive filling material;

FIG. 18 is an anterior-posterior view of a vertebral body, partially broken away and in section, in which multiple expandable bodies, introduced using an ipsa posterolateral access, have formed multiple separate cavities to receive filling material;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification describes new systems and methods to treat bones using expandable bodies. The use of expandable bodies to treat bones is disclosed in U.S. Pat. Nos. 4,969,888 and 5,108,404, which are incorporated herein by reference. Improvements in this regard are disclosed in U.S. patent application, Ser. No. 08/188,224, filed Jan. 26, 1994; U.S. patent application Ser. No. 08/485,394, filed Jun. 7, 1995; and U.S. patent application Ser. No. 08/659,678, filed Jun. 5, 1996, which are each incorporated herein by reference.

The new systems and methods will be first described with regard to the treatment of vertebra. It should be appreciated, however, the systems and methods so described are not limited in their application to vertebrae. As will be described in greater detail later, the systems and methods are applicable to the treatment of diverse bone types.

I. Treatment of Vertebral Bodies

Figure 1:
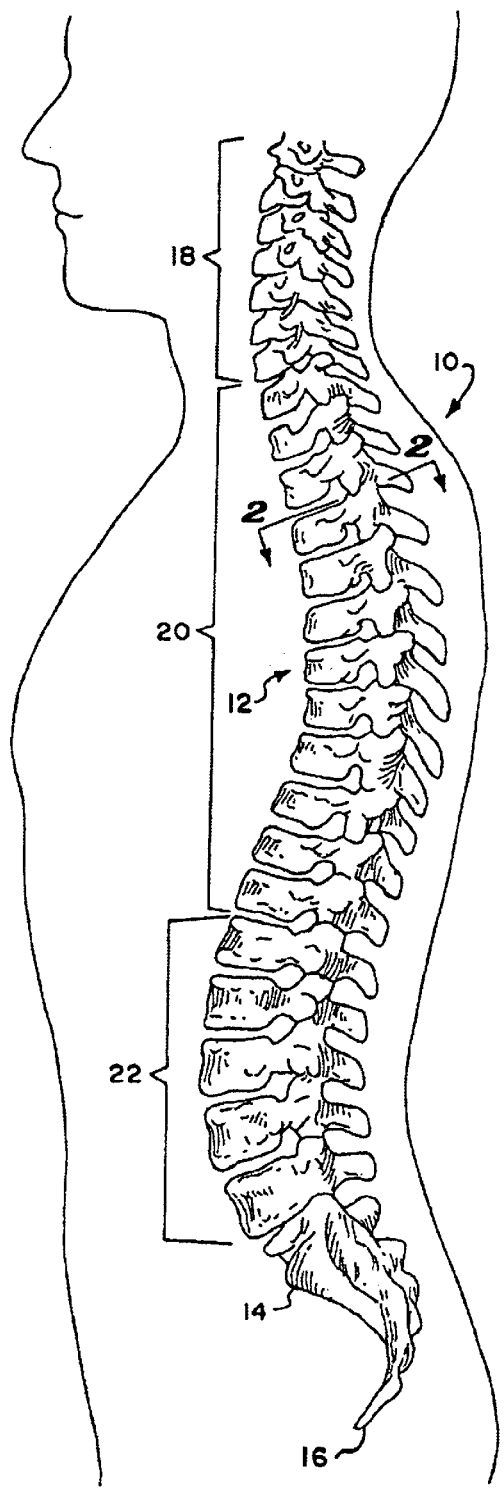
FIG. 1 is a side view of the spinal column of a human.

As FIG. 1 shows, the spinal column 10 comprises a number of uniquely shaped bones, called the vertebrae 12, a sacrum 14, and a coccyx 16(also called the tail bone). The number of vertebrae 12 that make up the spinal column 10 depends upon the species of animal. In a human (which FIG. 1 shows), there are twenty-four vertebrae 12, comprising seven cervical vertebrae 18, twelve thoracic vertebrae 20, and five lumbar vertebrae 22.

When viewed from the side, as FIG. 1 shows, the spinal column 10 forms an S-shaped curve. The curve serves to support the head, which is heavy. In four-footed animals, the curve of the spine is simpler.

Figure 2:
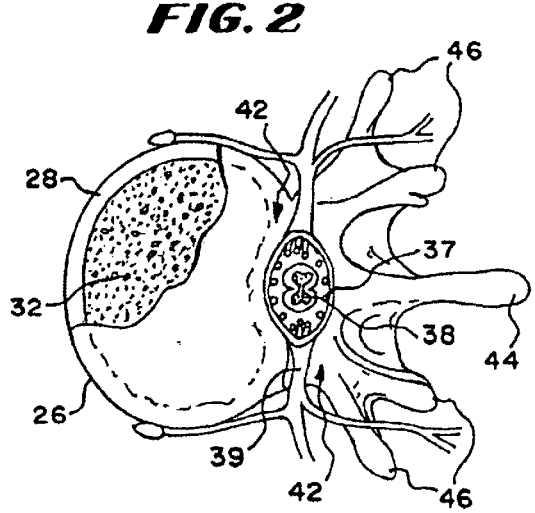
FIG. 2 is coronal view of a lumbar vertebra, partially cut away and in section, taken generally along line 2—2 in FIG. 1.
Figure 3:
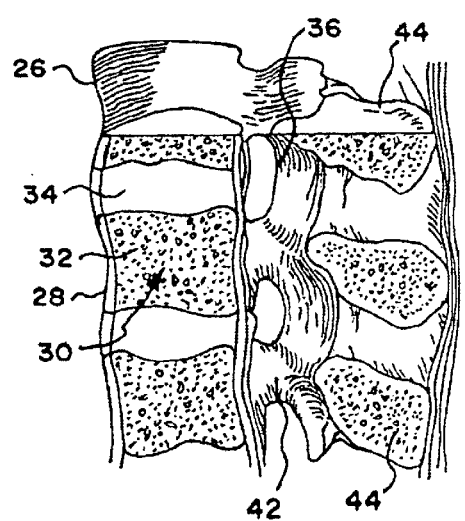
FIG. 3 is a vertical section of lumbar vertebrae.

As FIGS. 1 to 3 show, each vertebra 12 includes a vertebral body 26, which extends on the anterior (i.e., front or chest) side of the vertebra 12. As FIGS. 1 to 3 show, the vertebral body 26 is in the shape of an oval disk. As FIGS. 2 and 3 show, the vertebral body 26 includes an exterior formed from compact cortical bone 28. The cortical bone 28 encloses an interior volume 30 of reticulated cancellous, or spongy, bone 32(also called medullary bone or trabecular bone). A "cushion," called an intervertebral disk 34, is located between the vertebral bodies 26.

An opening, called the vertebral foramen 36, is located on the posterior (i.e., back) side of each vertebra 12. The spinal ganglion 39 pass through the foramen 36. The spinal cord 38 passes through the spinal canal 37.

The vertebral arch 40 surrounds the spinal canal 37. The pedicle 42 of the vertebral arch 40 adjoins the vertebral body 26. The spinous process 44 extends from the posterior of the vertebral arch 40, as do the left and right transverse processes 46.

A. Deployment of an Expandable Body

Figure 4:
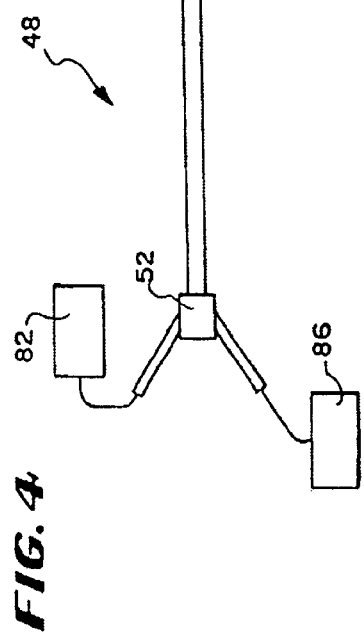
FIG. 4 is a plan view of a probe including a catheter tube carrying an expandable body intended to treat bone.

FIG. 4 shows a tool 48 for preventing or treating compression fracture or collapse of a vertebral body using an expandable body.

The tool 48 includes a catheter tube 50 having a proximal and a distal end, respectively 52 and 54. The distal end 54 carries an expandable body 56.

The body 56 includes an exterior wall 58, which, in FIG. 4, is shown in a collapsed geometry. The collapsed geometry permits insertion of the body 56 into the interior volume 30 of a targeted vertebral body 26.

The insertion of the body 56 into the interior volume 30 of a targeted vertebral body 26 can be accomplished in various ways. FIGS. 5A to 5Q show the insertion of the body 56 using a transpedicular approach, which can be performed either with a closed, mininimally invasive procedure or with an open procedure.

In the described procedure, a patient lies on an operating table, while the physician introduces a conventional spinal needle assembly 60 into soft tissue in the patient's back. The patient can lie facedown on the table, or on either side, or at an oblique angle, depending upon the physician's preference. Indeed, the procedure can be performed through an open anterior procedure or an endoscopic anterior procedure, in which case the tool 48 may be introduced from the anterior aspect of the vertebral body.

The spinal needle assembly 60 comprises a stylet 62 slidable housed within a stylus 64. The assembly 60 typically has, for example, about an 18 gauge diameter. Other gauge diameters can and will be used to accommodate appropriate guide pins, as will be described in greater detail later.

Under radiologic, CT, or MRI monitoring, the physician advances the assembly 60 through soft tissue (designated S in FIG. 5A) down to and into the targeted vertebra 12, as FIG. 5A shows. The physician will typically administer a local anesthetic, for example, lidocaine, through assembly 60. In some cases, the physician may prefer other forms of anesthesia.

The physician directs the spinal needle assembly 60 to penetrate the cancellous bone 32 of the targeted vertebra 12. Preferably the depth of penetration is about 60% to 95% of the vertebral body 26.

FIG. 5A shows gaining access to cancellous bone 32 through the pedicle 42, which is called transpedicular access. However, posterolateral access, through the side of the vertebral body 12 (designated P–L and shown in phantom lines in FIG. 5A), may be indicated, if a compression fracture has collapsed the vertebral body 26 below the plane of the pedicle 42, or for other reasons based upon the preference of the physician.

Figure 5B:
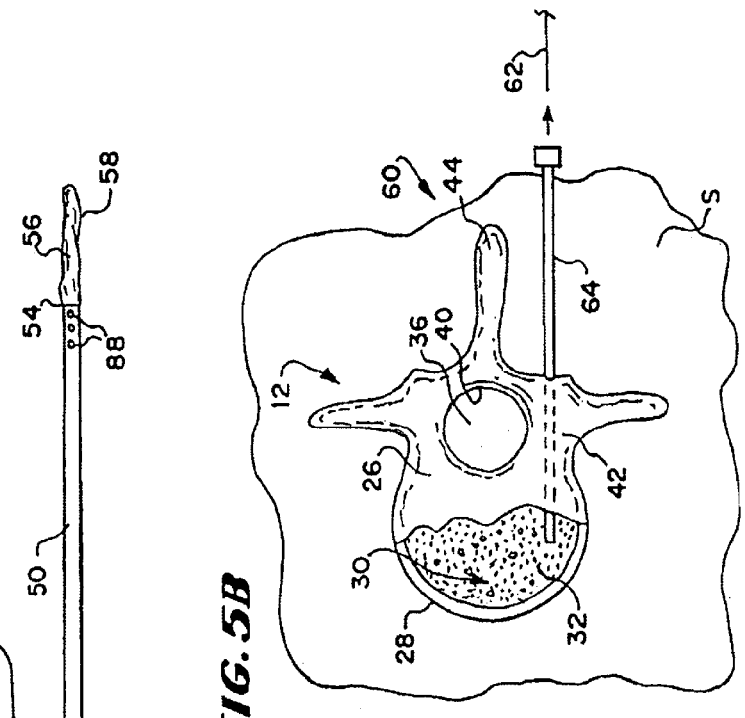
FIGS. 5A to 5P are a series of coronal views of a vertebra, partially cut away and in section, showing the steps of introducing, via transpedicular access, an expandable body to compress cancellous bone and create a cavity within a vertebral body, and of then conveying a filling material into the cavity to restore interior integrity to cortical bone.
FIG. 5Q is a lateral view, with parts broken away, of the vertebra shown in coronal view in FIG. 5P.
Figure 5A:
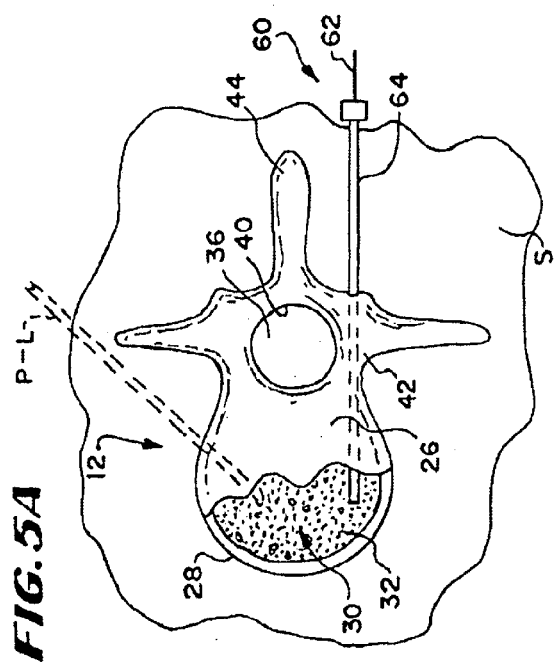

After positioning the spinal needle assembly 60 in cancellous bone 32, the physician holds the stylus 64 and withdraws the stylet 62 (see FIG. 5B). Still holding the stylus 64, the physician slides a guide pin 66 through the stylus 64 and into the cancellous bone 32(see FIG. 5C). The physician now removes the stylus 64, leaving the guide pin 66 deployed within the cancellous bone 32, as FIG. 5D shows.

As FIG. 5E shows, the physician makes a small incision (designated I in FIG. 5E) in the patient's back to accommodate a trocar 68. The physician inserts the trocar 68 through the soft tissue S along the guide pin 66 down to the pedicle 42. The physician taps the distal end 70 of the trocar 68 into the pedicle 42 to secure its position.

As FIG. 5F shows, the physician next slides an outer guide sheath 72 over the trocar 68. The distal end 74 of the outer guide sheath 72 is likewise tapped into the pedicle 42. The physician removes the trocar 68, leaving the guide pin 66 and outer guide sheath 72 in place, as FIG. 5G shows. Alternatively, the trocar 68 and guide sheath 72 can be introduced together in one step.

As FIG. 5H shows, the physician advances a drill bit 76 (for example, 5 mm in diameter) over the guide pin 66 through the outer guide sheath 72. Under X-ray control (or using another external visualizing system), the physician operates the drill bit 76 to open a passage 78 through the pedicle 42 and into the cancellous bone 32. The drilled passage 78 preferable extends no more than 95% across the vertebral body 26.

As FIG. 5I shows, the physician removes drill bit 76 and guide pin 66, leaving the outer guide sheath 72. The passage 78 made by the drill bit 76 remains, passing through the pedicle 42 and into the cancellous bone 32.

As FIG. 5J(1) shows, the physician next advances the catheter tube 50 and expandable body 56 through the outer guide sheath 72 and into the drilled passage 78 in the cancellous bone 32. As best shown in FIG. 5J(2), the body 56 is maintained in a straightened, collapsed condition distally beyond the end of the catheter tube 50 during transport through the guide sheath 72 and into the drilled passage 78 by a generally rigid, external protective sleeve 73, which surrounds the body 56. Alternatively, an internal stiffening member (not shown) can extend within the body 56, to keep the body 56 in the desired distally straightened condition during passage through the guide sheath 72. Once the body 56 is located in the desired location within the passage 78, the physician pulls the sleeve 73 back, to uncover the body 56. The expandable body 56 can be dipped into thrombin prior to its introduction into the vertebral body 26 to facilitate in situ coagulation.

The materials for the catheter tube 50 are selected to facilitate advancement of the body 56 into cancellous bone through the guide sheath 72. The catheter tube 50 can be constructed, for example, using standard flexible, medical grade plastic materials, like vinyl, nylon, polyethylenes, ionomer, polyurethane, and polyethylene tetraphthalate (PET). The catheter tube 50 can also include more rigid materials to impart greater stiffness and thereby aid in its manipulation. More rigid materials that can be used for this purpose include Kevlar™ material, PEBAX™ material, stainless steel, nickel-titanium alloys (Nitinol™ material), and other metal alloys.

Once the protective sheath 73 is withdrawn, the wall 58 of the body 56 is capable of assuming an expanded geometry within the interior volume 30(generally shown in FIG. 5K(1)). To accommodate expansion of the body 56, the catheter tube 50 includes a first interior lumen 80 (see FIG. 4). The lumen 80 is coupled at the proximal end of the catheter tube 50 to a pressurized source of fluid 82. The fluid 82 is preferably radio-opaque to facilitate visualization. For example, Renograffin™ can be used for this purpose.

The lumen 80 conveys the fluid 82 into the body 56 under pressure. As a result, the wall 58 expands, as FIG. 5K(1) shows. Because the fluid 82 is radio-opaque, body expansion can be monitored fluoroscopically or under CT visualization. Using real time MRI, the body 56 may be filled with sterile water, saline solution, or sugar solution.

Expansion of the wall 58 enlarges the body 56 and compacts cancellous bone 32 within the interior volume 30. As FIG. 5K(2) shows, the presence of the sheath 73 serves to keep the proximal end of the body 56 away from edge-contact with the distal end of the catheter tube 50.

The compaction of cancellous bone 32 forms a cavity 84 in the interior volume 30 of the vertebral body 26. The compaction of cancellous bone also exerts interior force upon cortical bone, making it possible to elevate or push broken and compressed bone back to or near its original prefracture position. Using a single transpedicular access (as FIG. 5K(1) shows), the cavity 84 occupies about one-half of the interior volume 30. As will be described in greater detail later, using multiple accesses, e.g., one through each pedicle, a cavity 84 occupying substantially all of the interior volume 30 can be created.

As FIG. 4 shows, the proximal end of the catheter tube 50 is preferably coupled by tubing to a source of negative air pressure 86. The negative pressure is conveyed through a second interior lumen 81 to one or more suction holes 88 on the distal end of the catheter tube 50. Prior to and during the expansion of the body 56, suction is applied to remove fats and other debris through the suction holes 88 for disposal. A separate suction-irrigation tool can be deployed through the guide sheath 72 for this purpose, if desired.

The body 56 is preferably left inflated for an appropriate waiting period, for example, three to five minutes, to allow coagulation inside the vertebral body 26. After the appropriate waiting period, the physician collapses the body 56 and removes it through the outer guide sheath 72 (see FIG. 5L). To facilitate removal, the exterior surface of the body 56 can be treated, e.g., by ion beam-based surface treatment, to reduce friction during passage through the outer guide sheath 72. As FIG. 5L shows, upon removal of the body 56, the formed cavity 84 remains in the interior volume 30.

A suction-irrigation tool (not shown) can be introduced through the outer guide sheath 72, to further flush and clear debris from the formed cavity 84 after removal of the body 56.

As FIG. 5M shows, an injector nozzle or tip 90, coupled by an injector tube 92 to an injector gun 94, is inserted through the outer guide sheath 72 into the formed cavity 84. The injector gun 94 carries a filling material 96. The filling material 96 comprises, for example, methylmethacrylate cement or a synthetic bone substitute.

The injector gun 94 can comprise a cement gun made, for example, by Stryker Corporation (Kalamazoo, Mich.). This particular injector gun 94 has a manually operated injection grip 98 with a mechanical advantage of about 9 to 1. Other injection guns may be used, having more or less mechanical advantage. Non-manually operated injection guns can also be used.

The injector tip 90 can be, for example, about 4.9 mm in diameter, to accommodate the flow a relatively viscous material 96 into the cavity 84.

As FIG. 5M shows, the injector gun 94 pushes the filling material 96 into the cavity 84. While injecting the material 96, the physician preferably begins with the injector tip 90 positioned at the anterior region of the cavity 84 (as FIG. 5M shows). The physician progressively moves the tip 90 toward the posterior region of the cavity 84 (as FIG. 5N shows), away from the flow of the material 96 as it enters and fills the cavity 84. The physician observes the progress of the injection fluoroscopically.

The physician can also check, using, for example, x-ray, for leakage of the material through cortical bone 28. Systems and methods for impeding or preventing such leakage will be described in greater detail later.

Figure 5P:
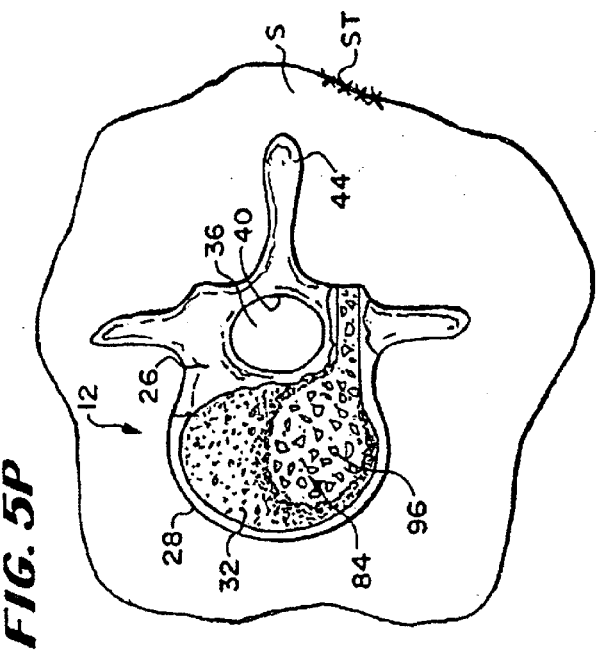
Figure 5Q:
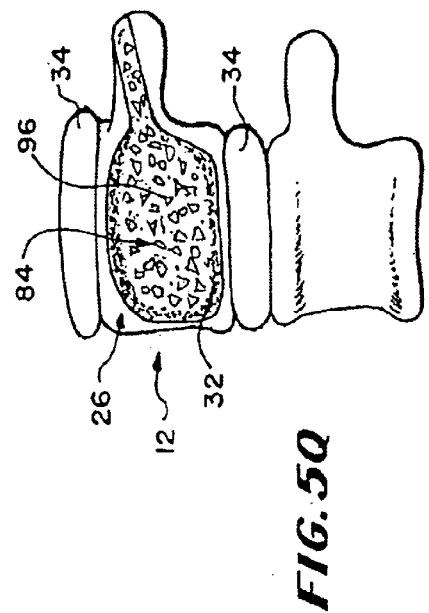
Figure 5O:
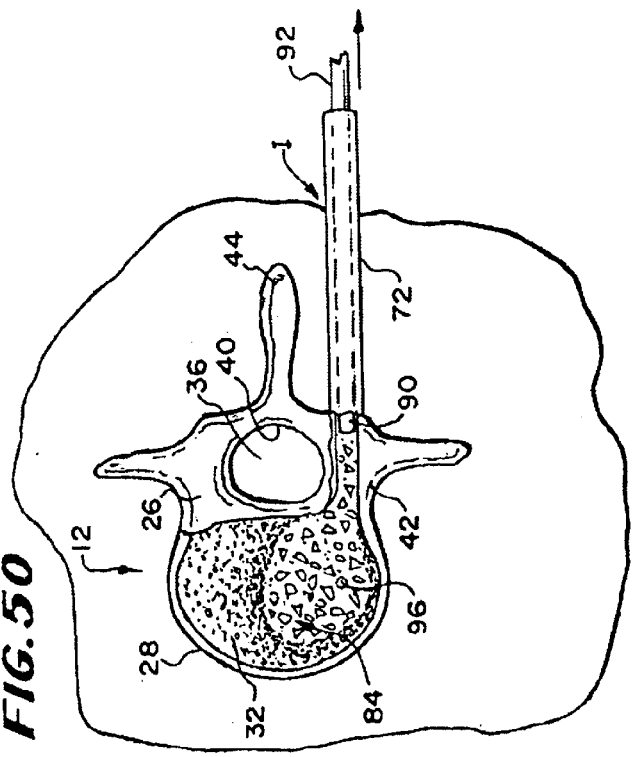

The physician flows material 96 into the cavity 84, until the material 96 reaches the distal end 74 of the outer guide sheath 72 (as FIG. 5O shows).

Upon removing the injector tube 92 from the outer guide sheath 72, the physician may, if necessary, tamp residual filling material 96 from the distal end 74 of the outer guide sheath 72 into the cavity 84. If fluoroscopic examination reveals void regions in the cavity 84, the physician may again insert the injector tube 92 to add more filling material 96 into the cavity 84.

Figure 7:
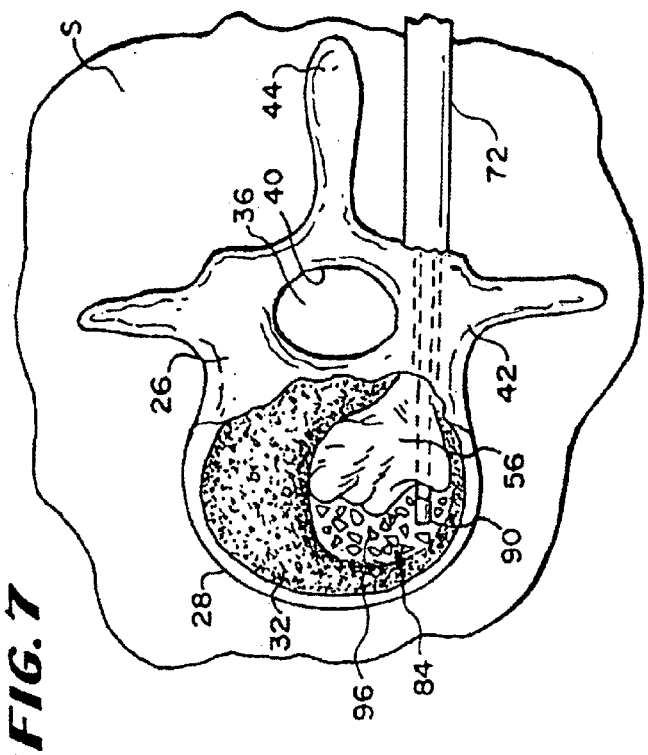
FIG. 7 is a coronal view, partially broken away and in section, of a vertebral body in which an expandable body is being collapsed after having formed a cavity, while an injector tip, also within the vertebral body, is simultaneously injecting filling material into the cavity.

FIG. 7 shows an alternative technique for filling the cavity. In this technique, the injector tip 90 occupies the cavity 84 while the expandable body 56 is collapsing within the cavity 84. As the body 56 collapses, the tip 90 injects material 96 into the part of the cavity 84 that the collapsing body 56 no longer occupies. The increasing volume of the cavity 84 not occupied by the collapsing body 56 is thereby progressively filled by an increasing volume of material 96. The presence of the body 56, partially expanded while the tip 90 injects the material 96, serves to compact and spread the injected material 96 within the cavity 84.

As filling of the cavity 84 progresses, preferably under fluoroscopic monitoring, the physician progressively retracts the injector tip 90 from the anterior region of the cavity 84, toward the outer guide sheath 72, allowing the material 96 to progressively enter and fill the cavity 84 with the collapse of the body 56.

Figure 8B:
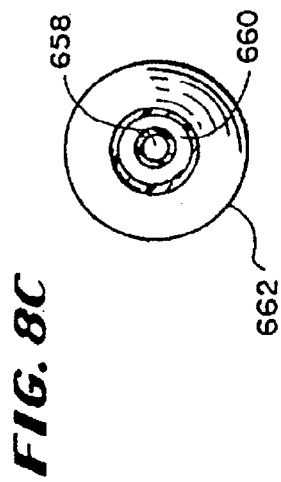
FIG. 8B is a side view of the tool shown in FIG. 8A, located outside bone.
Figure 8C:
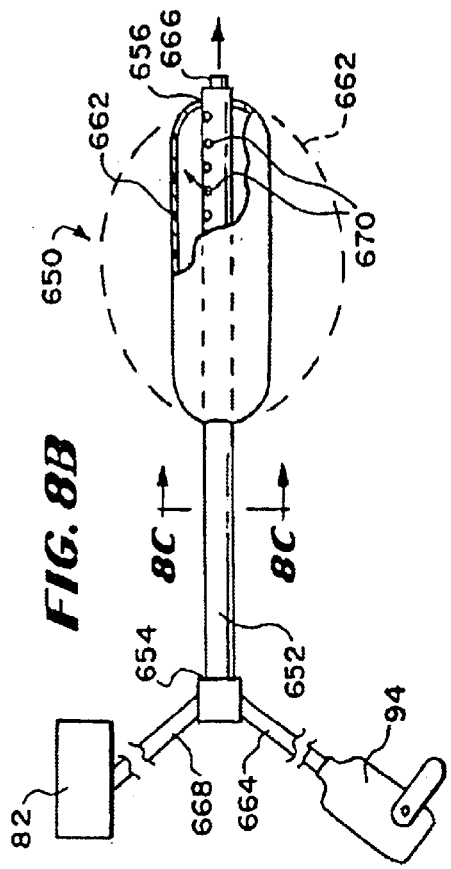
FIG. 8C is sectional view of the tool shown in FIG. 8B, taken generally along line 8C—8C in FIG. 8B.
Figure 8A:
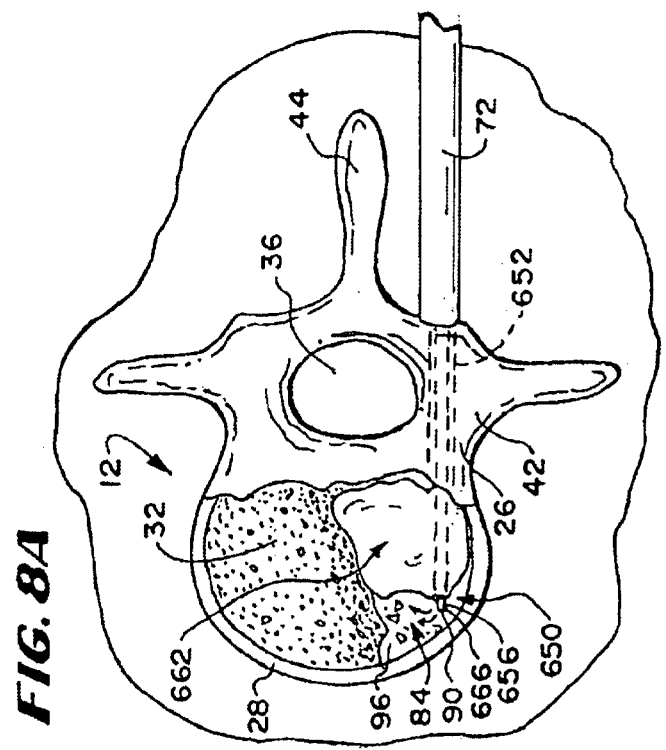
FIG. 8A is a coronal view of a vertebral body, partially broken away and in section, showing a tool that integrates an injector tube and an integral expandable body to create a cavity in cancellous bone, and also showing the injection of filling material simultaneous with collapse of the expandable body.

FIGS. 8A to 8C show a preferred embodiment of a tool 650 which integrates the injection tube and expandable body in a single structure. As FIG. 8B shows, the tool 650 includes a catheter tube 652 having a proximal end 654 and a distal end 656. The distal end carries an expandable body 662.

As FIG. 8C shows, the catheter tube 652 has concentric inner and outer lumens, respectively 658 and 660. The inner lumen 658 communicates, by proximal tubing 664, with an injector gun 94, of the type previously described. The inner lumen 658 also communicates with an injector nozzle or tip 666 at the distal catheter tube end 656. Operation of the gun 94 serves to inject filling material 96 through the nozzle 666 (as FIG. 8A shows).

The outer lumen 660 communicates, via proximal tubing 668, with a source 82 of pressurized liquid. The outer lumen 660 also communicates with ports 670 formed on the distal catheter tube end 656 underlying the expandable body 662. Operation of the source 82 serves to inject pressurized liquid into the body 662 to expand it, in the manner previously described.

As FIG. 8A shows, the physician introduces the tool 650 into the cancellous bone 32. The physician expands the body 662 to create the cavity 84. Once the cavity 84 is formed, the physician begins to collapse the body 662, while injecting the filling material 96 through the nozzle 666. The volume of the cavity 84 occupied by the collapsing body 662 is progressively filled by the increasing volume of filling material 96 injected through the nozzle 666.

As earlier described, the collapsing body 662 serves to compact and spread the filling material 96 more uniformly within the cavity 84. Under fluoroscopic monitoring, the physician progressively retracts the distal end 656 of the tool 650 from the anterior region of the cavity 84 toward the outer guide sheath 72, allowing the material 96 to enter and fill the cavity 84.

Upon filling the cavity 84 with the material 96, the physician removes the outer guide sheath 72, as FIGS. 5P and 5Q show. The incision site is sutured or otherwise closed (designated by ST in FIG. 5P).

In time, the filling material 96 sets to a hardened condition within the cavity 84 (see FIGS. 5P and 5Q). The hardened material 96 provides renewed interior structural support for the cortical bone 28.

The above described procedure, carried out in a minimally invasive manner, can also be carried out using an open surgical procedure. Using open surgery, the physician can approach the bone to be treated as if the procedure is percutaneous, except that there is no skin and other tissues between the surgeon and the bone being treated. This keeps the cortical bone as intact as possible, and can provide more freedom in accessing the interior volume 30 of the vertebral body.

B. Material Selection for the Expandable Body

The material of the body wall 58 can be selected according to the therapeutic objectives surrounding its use. For example, materials including vinyl, nylon, polyethylenes, ionomer, polyurethane, and polyethylene tetraphthalate (PET) can be used. The thickness of the body wall 58 is typically in the range of $2/1000$ths to $25/1000$ths of an inch, or other thicknesses that can withstand pressures of up to, for example, 250–500 psi.

If desired, the material for the wall 58 can be selected to exhibit generally elastic properties, like latex. Alternatively, the material can be selected to exhibit less elastic properties, like silicone. Using expandable bodies 56 with generally elastic or generally semi-elastic properties, the physician monitors the expansion to assure that over-expansion and wall failure do not occur. Furthermore, expandable bodies 56 with generally elastic or generally semi-elastic properties will require some form of external or internal restraints to assure proper deployment in bone.

Figure 6:
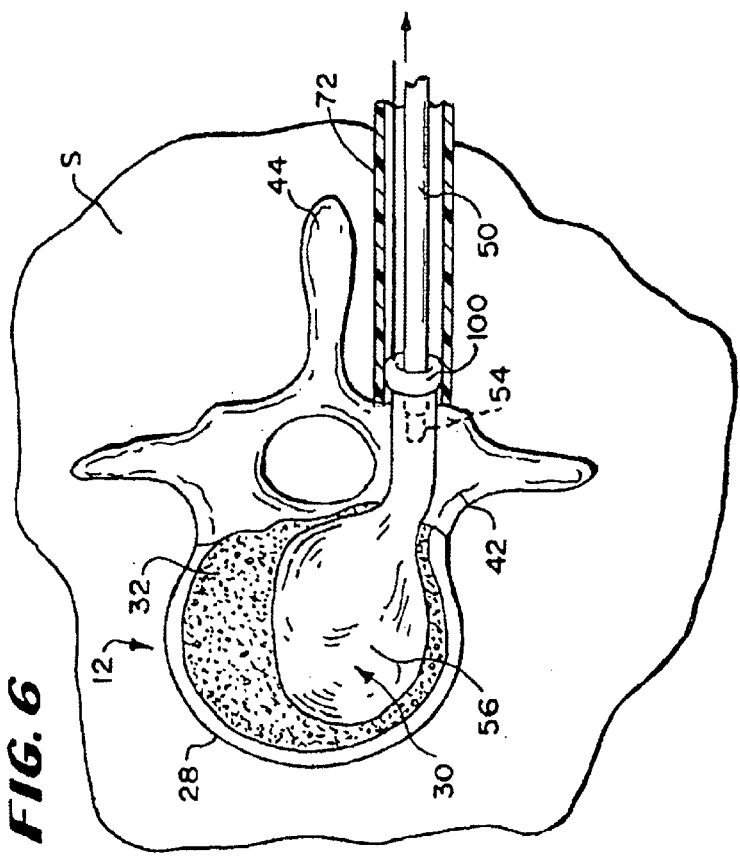
FIG. 6 is a coronal view of a vertebral body in which an expandable body, restrained by an external sealing element, compresses cancellous bone to form a cavity.

For example, expandable bodies 56 with generally elastic properties will exhibit the tendency to backflow or creep into the outer guide sheath 72 during their expansion. It is therefore necessary to internally or externally restrain a body 56 that is subject to creeping, to keep it confined within the interior bone region. In FIG. 6, an exterior sealing element 100 is provided for this purpose. In FIG. 6, the sealing element 100 takes the form of a movable o-ring.

The physician advances the o-ring 100 along the catheter tube 50 inside the guide sheath 72 using a generally stiff stylet 102 attached to the o-ring 100. The physician locates the o-ring 100 at or near the distal end 54 of the catheter tube 50 prior to conveying the liquid 82 to expand the body 56. The o-ring 100 is held in place by the generally stiff stylet 102, which provides a counter force to prevent backward movement of the o-ring 100 in the guide sheath 72 as the body 56 expands. The o-ring 100 thereby keeps all or a substantial portion of the generally elastic body 26 confined inside the interior volume 30. The body 56 thereby serves to compact as much of the cancellous bone 32 as possible.

The use of an external sealing element 100 to restrain the expandable body 56 may not be necessary when relatively inelastic materials are selected for the body 56. For example, the material for the body wall 58 can be selected to exhibit more inelastic properties, to limit expansion of the wall 58 prior to wall failure. The body wall 58 can also include one or more restraining materials, particularly when the body wall 58 is itself made from more elastic materials. The restraints, made from flexible, inelastic high tensile strength materials, limit expansion of the body wall 58 prior to wall failure. Representative examples of generally inelastic wall structures will be described in greater detail later.

C. Selection of Shape and Size for the Expandable Body

As will also be demonstrated later, when relatively inelastic materials are used for the body wall 58, or when the body wall 58 is otherwise externally restrained to limit its expansion prior to failure, a predetermined shape and size can be imparted to the body 56, when it is substantially expanded. The shape and size can be predetermined according to the shape and size of the surrounding cortical bone 28 and adjacent internal structures, or by the size and shape of the cavity 84 desired to be formed in the cancellous bone 32.

In one embodiment, which is generally applicable for treating bones experiencing or prone to fracture, the shape and size of the body 56, when substantially expanded, can be designed to occupy at least about 30% of the volume of cancellous bone 32 in the interior volume 30. A body 56 having a substantially expanded size and shape in the range of about 40% to about 99% of the cancellous bone volume is preferred.

In another embodiment, which is applicable for treating bones having more localized regions of fracture or collapse caused, for example, by avascular necrosis, the shape and size of the body 56 can be designed to occupy as little as about 10% of the cancellous bone volume. In this embodiment, the drilled passage 78 extends directly to the localized site of injury, to enable targeted introduction of the body 26.

The shape of the cancellous bone 32 to be compressed, and the presence of surrounding local anatomic structures that could be harmed if cortical bone were moved inappropriately, are generally understood by medical professionals using textbooks of human skeletal anatomy, along with their knowledge of the site and its disease or injury. The physician is also able to select the materials and geometry desired for the body 56 based upon prior analysis of the morphology of the targeted bone using, for example, plain films, spinous process percussion, or MRI or CRT scanning. The materials and geometry of the body 56 are selected to create a cavity 84 of desired size and shape in cancellous bone 32 without applying harmful pressure to the outer cortical bone 28 or surrounding anatomic structures.

In some instances, it is desirable, when creating the cavity 84, to move or displace the cortical bone 28 to achieve the desired therapeutic result. Such movement is not per se harmful, as that term is used in this Specification, because it is indicated to achieve the desired therapeutic result. By definition, harm results when expansion of the body 56 results in a worsening of the overall condition of the bone and surrounding anatomic structures, for example, by injury to surrounding tissue or causing a permanent adverse change in bone biomechanics.

D. Deployment of Multiple Expandable Bodies

Formation of a desired cavity geometry in cancellous bone 32 using an expandable body 56 can be accomplished in diverse ways to achieve the desired therapeutic effect. The foregoing disclosure envisions the deployment of a single expandable body 56 to compact cancellous bone 32 and, by itself, form a cavity 84 having a desired shape and size to receive a filling material 96.

Alternatively, a cavity 84 having a desired shape and size in cancellous bone 32 can be formed by the deployment of more than one expandable body 56 in a targeted region of cancellous bone 32, either sequentially or simultaneously.

FIG. 9 shows the representative deployment of multiple expandable bodies 56A and 56B through a single outer guide sheath 72, which is arranged to provide transpedicular access. It should be understood that deployment of multiple expandable bodies can likewise be achieved through an outer guide sheath 72 arranged to provide a posterolateral access, through the side of the vertebral body 26 (as shown as P–L in phantom lines in FIG. 9). In FIG. 9, the expandable bodies 56A and 56B are carried by separate catheter tubes 50A and 50B, which are not joined together.

In the alternative embodiment shown in FIG. 10, a tool 109 comprising an array 108 of catheter tubes 50A and 50B is provided. Each catheter tube 50A and 50B each carries an expandable body 56A and 56B, which are shown in FIG. 10 in a collapsed condition. In FIG. 10, the distal ends of the catheter tubes 50A and 50B are joined by a connector 106, for simultaneous deployment through an outer guide sheath 72 into the vertebral body 26, as FIG. 9 shows. As before described, a slidable protective sheath 73 encloses the bodies 56A and 56B during passage through the guide sheath 72. Upon withdrawal of the protective sheath 73, expansion of the bodies 56A and 56B, either simultaneously or sequentially, creates a cavity 84. If desired, the connector 106 can permit relative adjustment of the catheter tubes 50A and 50B, so that, when deployed, one expandable body is located more distal to another expandable body.

For the sake of illustration, FIGS. 9 and 10 show two catheter tubes 50A and 50B, but more than two catheter tubes can be deployed in the vertebral body 26, either as separate tools (as FIG. 9 shows), or joined to form a composite array 108 (as FIG. 10 shows).

In FIG. 10, the bodies 56A and 56B of the array 108 have generally the same geometry, when substantially expanded, thereby providing a symmetric arrangement for compacting cancellous bone 32. A generally symmetric cavity 84 results.

Alternatively, as shown in FIG. 11, the bodies 56A and 56B possess different geometries when substantially expanded, thereby presenting an asymmetric arrangement for compacting cancellous bone 32. A generally asymmetric cavity 84 results. By mutually adjusting catheter tubes through a connector 106 (as previously described), the distal extensions of expandable bodies relative to each other can be made to differ, thereby also resulting in asymmetric cavity formation.

The selection of size and shape of the array 108, whether symmetric or asymmetric, depends upon the size and shape of the targeted cortical bone 28 and adjacent internal structures, or by the size and shape of the cavity 84 desired to be formed in the cancellous bone 32. The deployment of multiple expandable bodies 56 makes it possible to form cavities 84 having diverse and complex geometries within bones of all types. Multiple expandable bodies having generally the same geometry can be deployed in different ways to create cavities of different geometries.

It should be appreciated that the various styles of multiple expandable bodies 56 shown in FIGS. 9 to 11 are deployed in a distally straightened condition (as FIGS. 10 and 11 show) by using, e.g., a relatively stiff, surrounding sheath 73 (shown in phantom lines in FIG. 10), which is manipulated in the same as previously described in connection with FIGS. 5J(1) and 5J(2). There are, of course, other ways to straighten the bodies 56 for deployment into bone, such as through the use of internal stiffening elements.

Access for expandable bodies 56 can be achieved through multiple access sites and in many different ways. For example, multiple expandable bodies can access the vertebral body from different regions of a targeted vertebra.

FIG. 12 shows a representative dual transpedicular access, in which two outer guide sheaths 72A and 72B are used to provide separate access for two or more expandable bodies 56A and 56B through different sides of the pedicle 42A and 42B of the vertebral body 26.

FIG. 13 shows a representative dual contra lateral posterolateral access, in which two outer guide sheaths 72A and 72B are used to provide separate access for multiple expandable bodies 56A and 56B from different lateral sides of the vertebral body 26.

Figure 15:
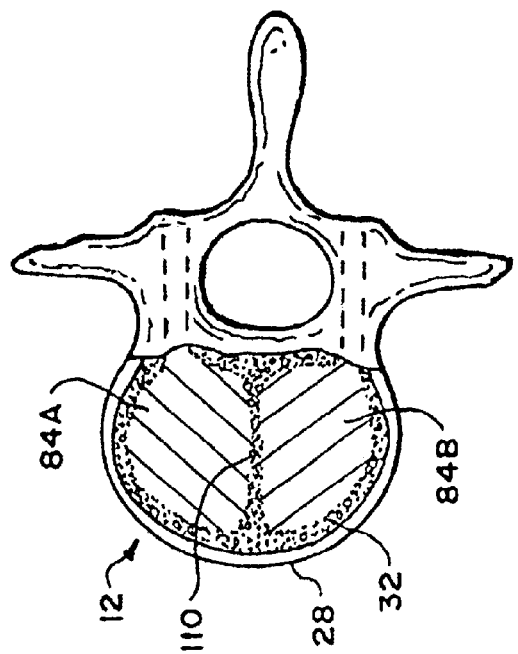
FIG. 15 is a coronal view of a vertebral body, partially broken away and in section, in which multiple expandable bodies have formed multiple separate cavities to receive filling material.
Figure 14:
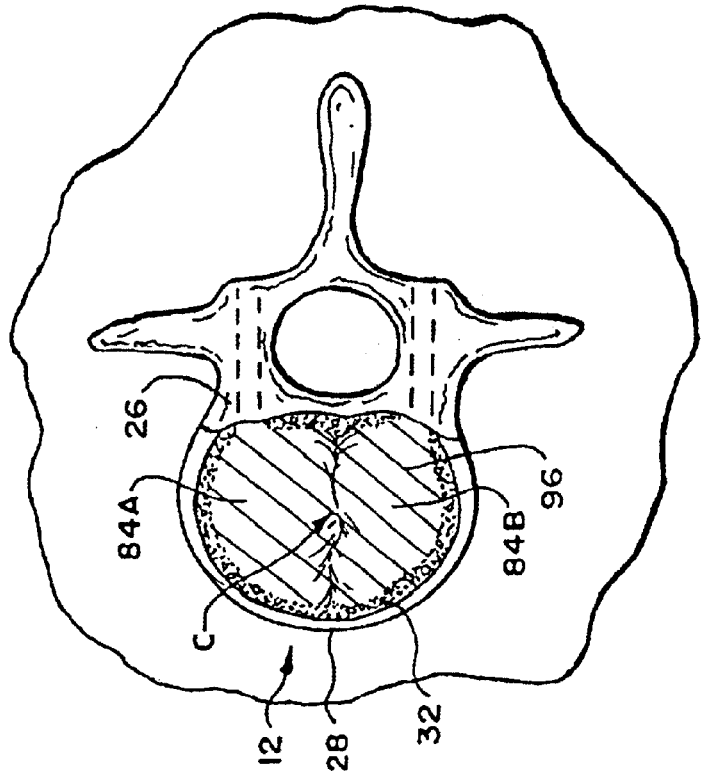
FIG. 14 is a coronal view of a vertebral body, partially broken away and in section, in which multiple expandable bodies have formed multiple cavities which join to form a single cavity to receive filling material.

Deployed from dual access sites as shown in FIGS. 12 and 13, the multiple expandable bodies 56A and 56B each forms a cavity 84A and 84B (shown in FIG. 14). The cavities 84A and 84B are transversely spaced within the cancellous bone 32. The transversely spaced cavities 84A and 84B may adjoin to form a single combined cavity (designated C in FIG. 14), into which the filling material 96 is injected. Alternatively, as FIG. 15 shows, the transversely spaced cavities 84A and 84B may remain separated by a region of cancellous bone (designated by numeral 110 in FIG. 13). In this arrangement, the filling material 96 is injected into multiple, individual cavities 84A and 84B within the interior volume.

As another example, multiple expandable bodies 56A and 56B can access the vertebral body 26 from the same general region of the vertebra. FIG. 16 shows a representative dual ipsilateral posterolateral access, in which two outer guide sheaths 72A and 72B are used to provide separate access from the same lateral sides of the vertebral body 26.

Deployed from these access sites (see FIG. 17), the multiple expandable bodies 56A and 56B form vertically spaced, or stacked, cavities 84A and 84B. The vertically spaced cavities 84A and 84B may adjoin to form a single combined cavity (designated C in FIG. 17), into which the filling material 96 is injected. Alternatively (see FIG. 18), the vertically spaced cavities 84A and 84B may be separated by a region of cancellous bone (designated by numeral 110 in FIG. 18), forming multiple individual cavities 84A and 84B within the interior volume, each of which is individually filled with a filling material 96A and 96B.

Figure 19:
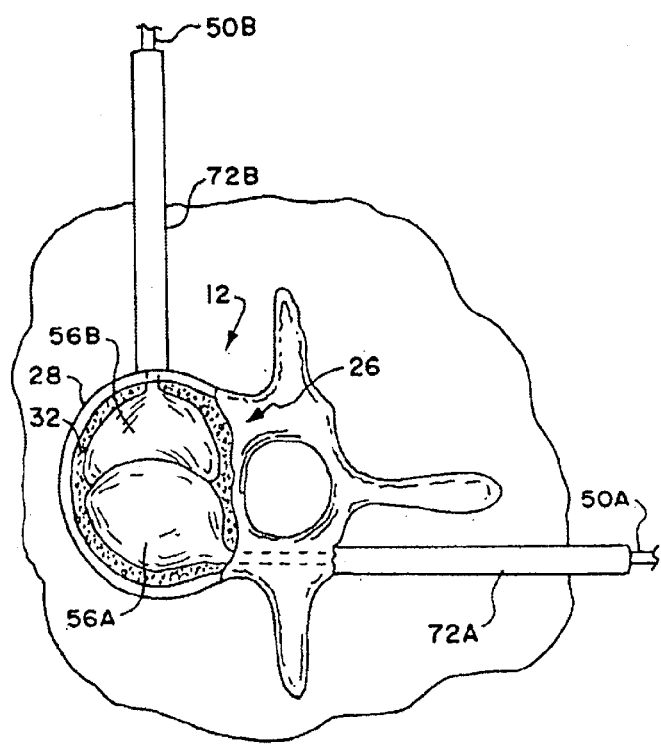
FIG. 19 is a coronal view of a vertebral body, partially broken away and in section, in which multiple expandable bodies have been introduced by both transpedicular and posterolateral access.

By way of another example, FIG. 19 shows a first outer guide sheath 72A arranged to provide a transpedicular access and a second outer guide sheath 72B to provide a posterolateral access.

Systems for treating bone using multiple expandable bodies can include directions 79 (see FIG. 12) for deploying the first and second expandable bodies. For example, the directions 79 can instruct the physician to insert a first expandable body into the interior volume through a first access path through cortical bone, while inserting a second expandable body into the interior volume through a second access path through cortical bone different than the first access path.

In any of the above-described examples, each guide sheath 72A or 72B can itself accommodate a single expandable body or multiple expandable bodies. The size and shape of the bodies may be the same, or they may vary, according to the desired objectives of the physician for the targeted vertebral body.

Figure 20:
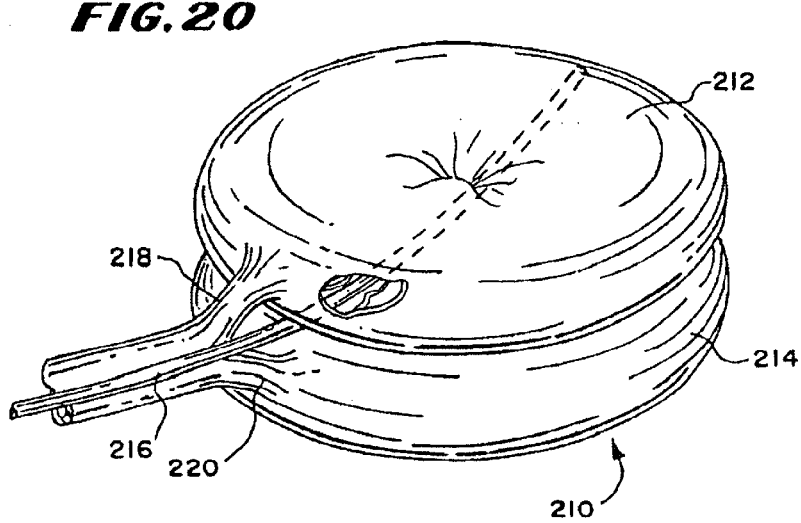
FIG. 20 is a perspective view of one representative embodiment of an expandable body having a stacked doughnut-shaped geometry.

E. Representative Embodiments of Expandable Bodies to Treat Vertebrae i. Constrained Donut-Shaped Geometries FIG. 20 shows a representative embodiment of an expandable body, which is broadly denoted by the numeral 210. The body 210 comprises a pair of hollow, inflatable, non-expandable parts 212 and 214 of flexible material, such as PET or Kevlar. Parts 12 and 14 have a suction tube 216 therebetween for drawing fats and other debris by suction into tube 216 for transfer to a remote disposal location. The catheter tube 216 has one or more suction holes so that suction may be applied to the open end of tube 216 from a suction source (not shown).

The parts 212 and 214 are connected together by an adhesive which can be of any suitable type. Parts 212 and 214 are doughnut-shaped, as shown in FIG. 20 and have tubes 218 and 220 which communicate with and extend away from the parts 212 and 214, respectively, to a source of inflating liquid under pressure (not shown). The liquid expands the body 210 as already described.

Figure 21:
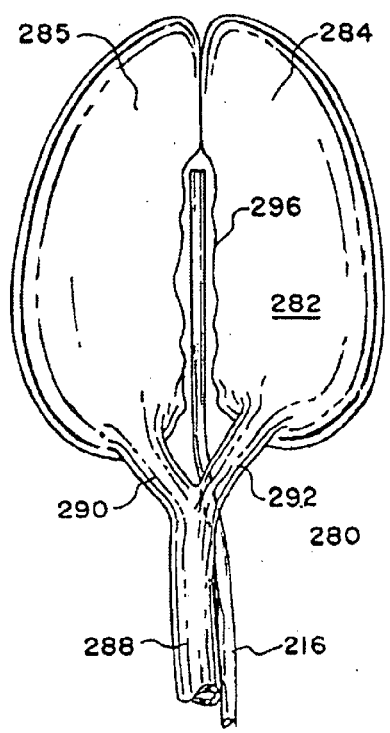
FIG. 21 is a view of another representative embodiment of an expandable body having an oblong-shaped geometry.

FIG. 21 shows a modified doughnut shape body 280 of the type shown in FIG. 20, except the doughnut shapes of body 280 are not stitched onto one another. In FIG. 21, body 280 has a pear-shaped outer convex surface 282 which is made up of a first hollow part 284 and a second hollow part 285. A tube 288 is provided for directing liquid into the two parts along branches 290 and 292 to inflate the parts after the parts have been inserted into the interior volume of a bone. A catheter tube 216 may or may not be inserted into the space 296 between two parts of the balloon 280 to provide irrigation or suction. An adhesive bonds the two parts 284 and 285 together.

Figure 22:
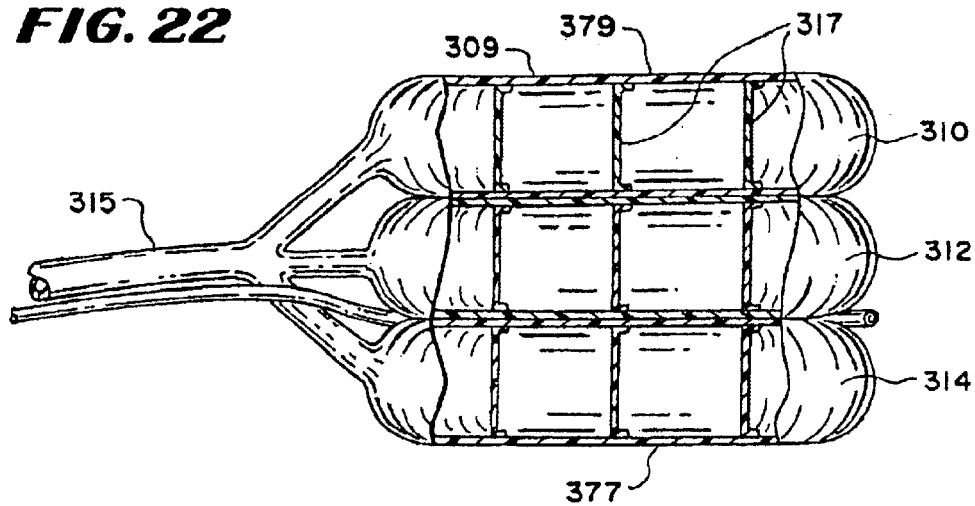
FIG. 22 is an elevation view of another representative embodiment of an expandable body showing three stacked bodies and string-like restraints for limiting the expansion of the bodies during inflation.

FIG. 22 shows another representative embodiment of an expandable body, designated 309. The body 309 has a generally round geometry and three expandable body units 310, 312 and 314. The body units 310, 312, and 314 include string-like external restraints 317, which limit the expansion of the body units 310, 312, and 314 in a direction transverse to the longitudinal axes of the body units 310, 312, and 314. The restraints 317 are made of the sane or similar material as that of the body units 310, 312, and 314, so that they have some resilience but substantially no expansion capability.

A tubes 315 direct liquid under pressure into the body units 310, 312 and 314 to expand the units and cause compaction of cancellous bone. The restraints 317 limit expansion of the body units prior to failure, keeping the opposed sides 377 and 379 substantially flat and parallel with each other.

ii. Constrained Kidney-Shaped Geometries

Figure 23:
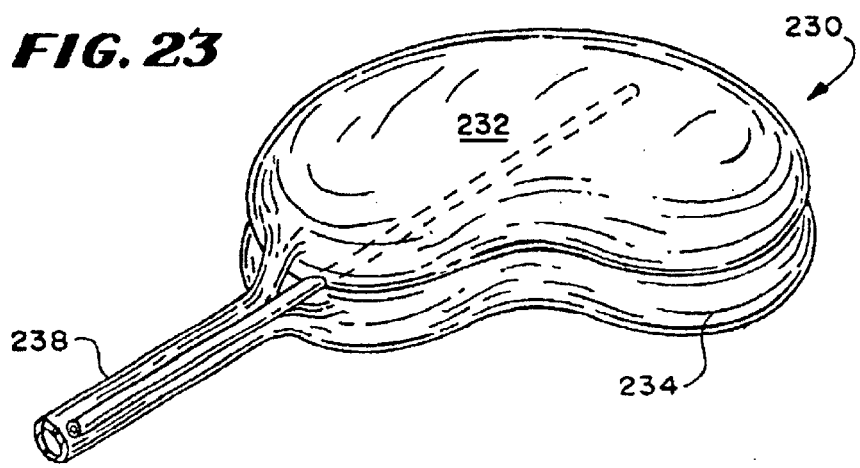
FIG. 23 is a perspective view of another representative embodiment of an expandable body having a kidney bean-shaped geometry.

FIG. 23 shows another representative embodiment of an expandable body 230, which has a kidney-shaped geometry. The body 230 has a pair of opposed kidney-shaped side walls 232 and a continuous end wall 234. A tube 238 directs liquid into the body to expand it within the vertebral body.

Figure 24:
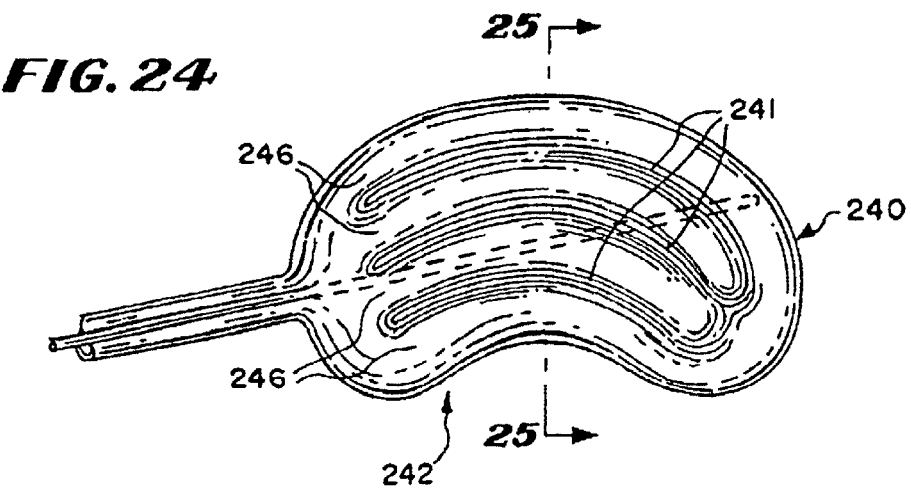
FIG. 24 is a top view of another representative embodiment of an expandable body having a kidney bean-shaped geometry with several compartments by a heating element or branding tool.
Figure 25:
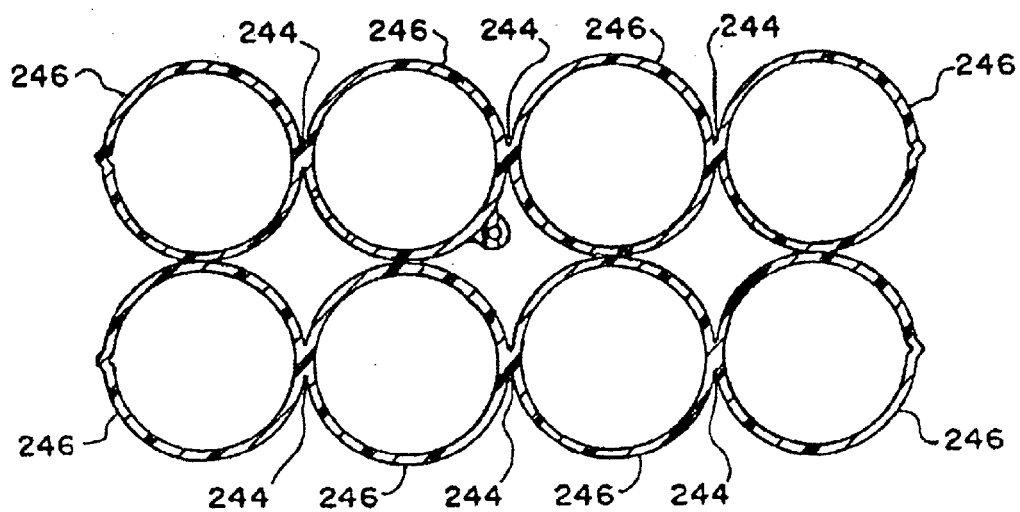
FIG. 25 is a cross-sectional view taken along line 25—25 of FIG. 24.

FIG. 24 shows another representative embodiment of an expandable body 242, which also has a kidney-shaped geometry. The body 242 is initially a single chamber bladder, but the bladder is branded along curved lines or strips 241 to form attachment lines 244 which take the shape of side-by-side compartments 246 which are kidney shaped as shown in FIG. 25. A similar pattern of strips as in 240 but in straight lines would be applied to a body that is square or rectangular. The branding causes a welding of the two sides of the bladder to occur.

The details of these and other expandable bodies usable to treat vertebral bodies are described in U.S. patent application, Ser. No. 08/188,224, filed Jan. 26, 1994, which is incorporated herein by reference.

F. Selection of Desired Geometry

The eventual selection of the size and shape of a particular expandable body or bodies to treat a targeted vertebral body 26 is based upon several factors. When multiple expandable bodies are used, the total combined dimensions of all expandable bodies deployed, when substantially expanded, should be taken into account.

Figure 26:
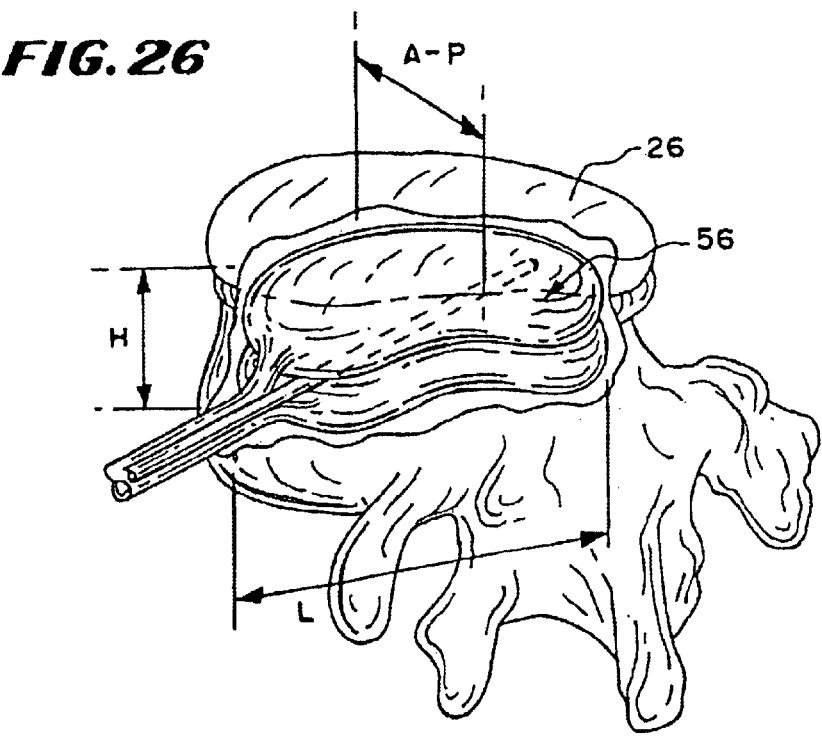
FIG. 26 is a perspective, lateral view of a vertebral body, partially broken away to show the presence of an expandable body, and also showing the major reference dimensions for the expandable body.

The anterior-posterior (A–P) dimension (see FIG. 26) for the expandable body or bodies is selected from the CT scan or plain film or x-ray views of the targeted vertebral body 26. The A–P dimension is measured from the internal cortical wall of the anterior cortex to the internal cortical wall of the posterior cortex of the vertebral body. In general, the appropriate A–P dimension for the expandable body or bodies is less than this anatomic measurement.

The appropriate side to side dimension L (see FIG. 26) for an expandable body or bodies is also selected from the CT scan, or from a plain film or x-ray view of the targeted vertebral body. The side to side distance is measured between the internal cortical walls laterally across the targeted vertebral body. In general, the appropriate side to side dimension L for the expandable body is less than this anatomic measurement.

The lumbar vertebral body tends to be much wider in side to side dimension L then in A–P dimension. In thoracic vertebral bodies, the side to side dimension and the A–P dimensions are almost equal.

The height dimensions H of the expandable body or bodies (see FIG. 26) is chosen by the CT scan or x-ray views of the vertebral bodies above and below the vertebral body to be treated. The height of the vertebral bodies above and below the vertebral body to be treated are measured and averaged. This average is used to determine the appropriate height dimension of the chosen expandable body.

The dimensions of expandable body or bodies for use in vertebrae are patient specific and will vary across a broad range, as summarized in the following table:

| Vertebra Type | Height (H) Dimension of Typical Expandable Body or Bodies | Posterior (A-P) Dimension of Typical Expandable Body or Bodies | Side to Side Dimension (L) of Typical Expandable Body or Bodies |
| --- | --- | --- | --- |
| Lumbar | 0.5 cm to 4.0 cm | 0.5 cm to 4.0 cm | 0.5 cm to 5.0 cm |
| Thoracic | 0.5 cm to 3.5 cm | 0.5 cm to 3.5 cm | 0.5 cm to 4.0 cm |

A preferred expandable body 56 for use in a vertebral body is stacked with two or more expandable members of unequal height (see FIG. 26), where each member can be separately inflated through independent tube systems. The total height of the stack when fully inflated should be within the height ranges specified above. Such a design allows the fractured vertebral body to be returned to its original height in steps, which can be easier on the surrounding tissue, and it also allows the same balloon to be used in a wider range of vertebral body sizes.

II. Treatment of Long Bones

Figure 43:
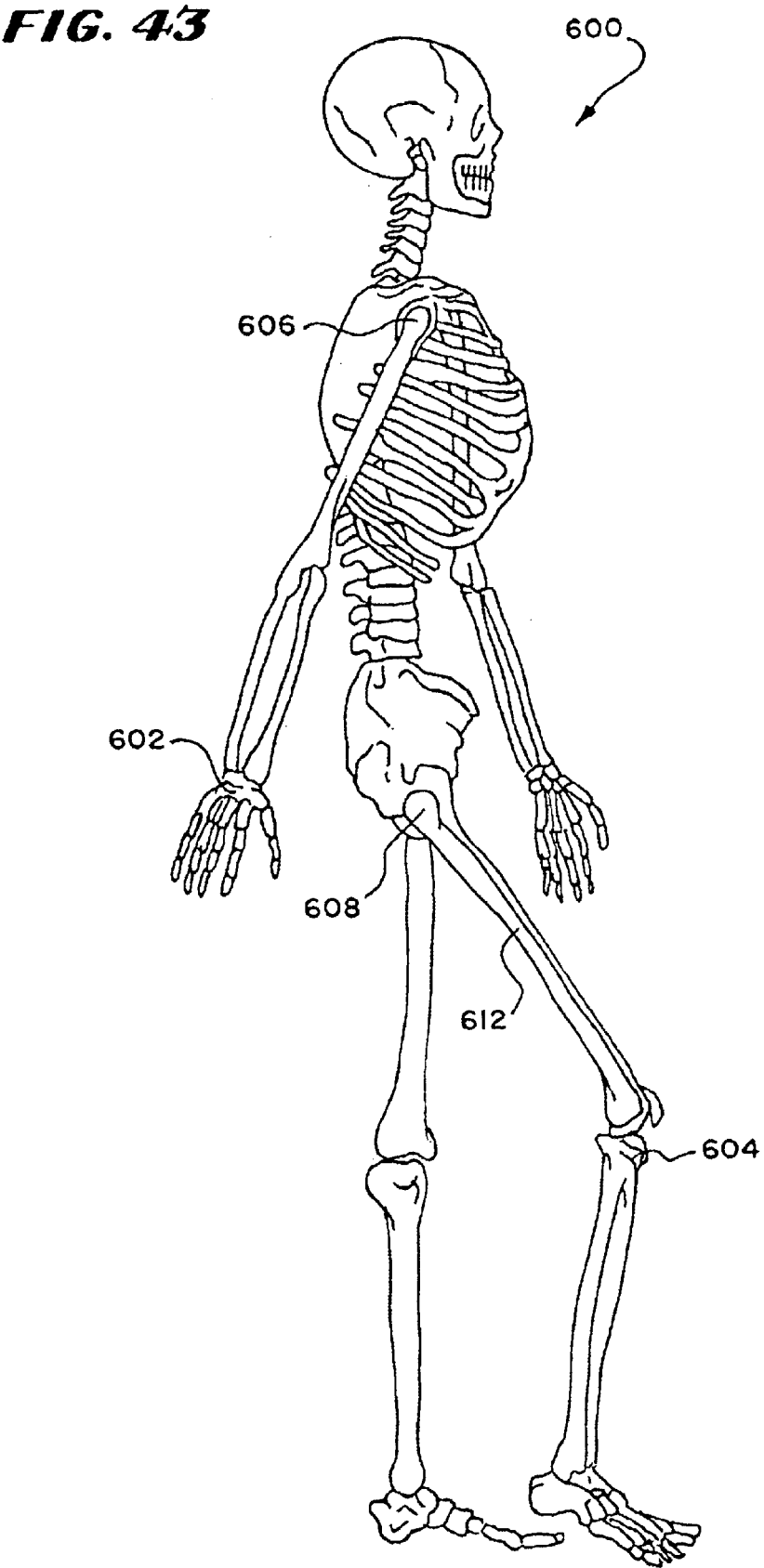
FIG. 43 is an illustration of the human skeleton, showing regions of long bone that can be treated using expandable bodies.

Like vertebrae, the interior regions of long bones substantially occupied by cancellous bone can be treated with the use of one or more expandable bodies. FIG. 43 shows representative regions of the human skeleton 600, where cancellous bone regions of long bones can be treated using expandable bodies. The regions include the distal radius (Region 602); the proximal tibial plateau (Region 604); the proximal humerus (Region 606); the proximal femoral head (Region 608); and the calcaneus (Region 610).

As for vertebral bodies, expandable bodies possess the important attribute of being able, in the course of forming cavities by compressing cancellous bone, to also elevate or push broken or compressed cortical bone back to or near its normal anatomic position. This is a particularly important attribute for the successful treatment of compression fractures or cancellous bone fractures in the appendicular skeleton, such as the distal radius, the proximal humerus, the tibial plateau, the femoral head, hip, and calcaneus.

Representative examples of expandable bodies for the treatment of cancellous bone regions of long bones will be next described.

A. Expandable Body for the Distal Radius

The selection of an appropriate expandable to treat a fracture of the distal radius (Region 602 in FIG. 43) will depend on the radiological size of the distal radius and the location of the fracture.

Figure 28:
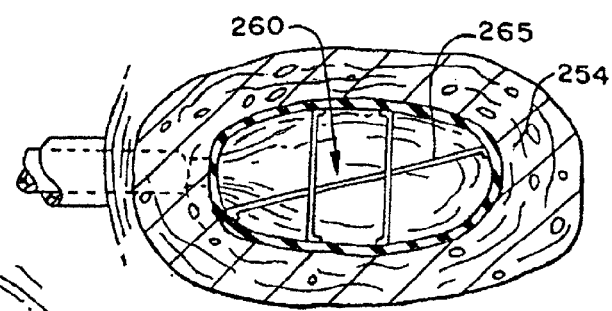
FIGS. 28 is a cross sectional view of the expandable body shown in FIG. 27, taken generally along line 28—28 of FIG. 27.
Figure 27:
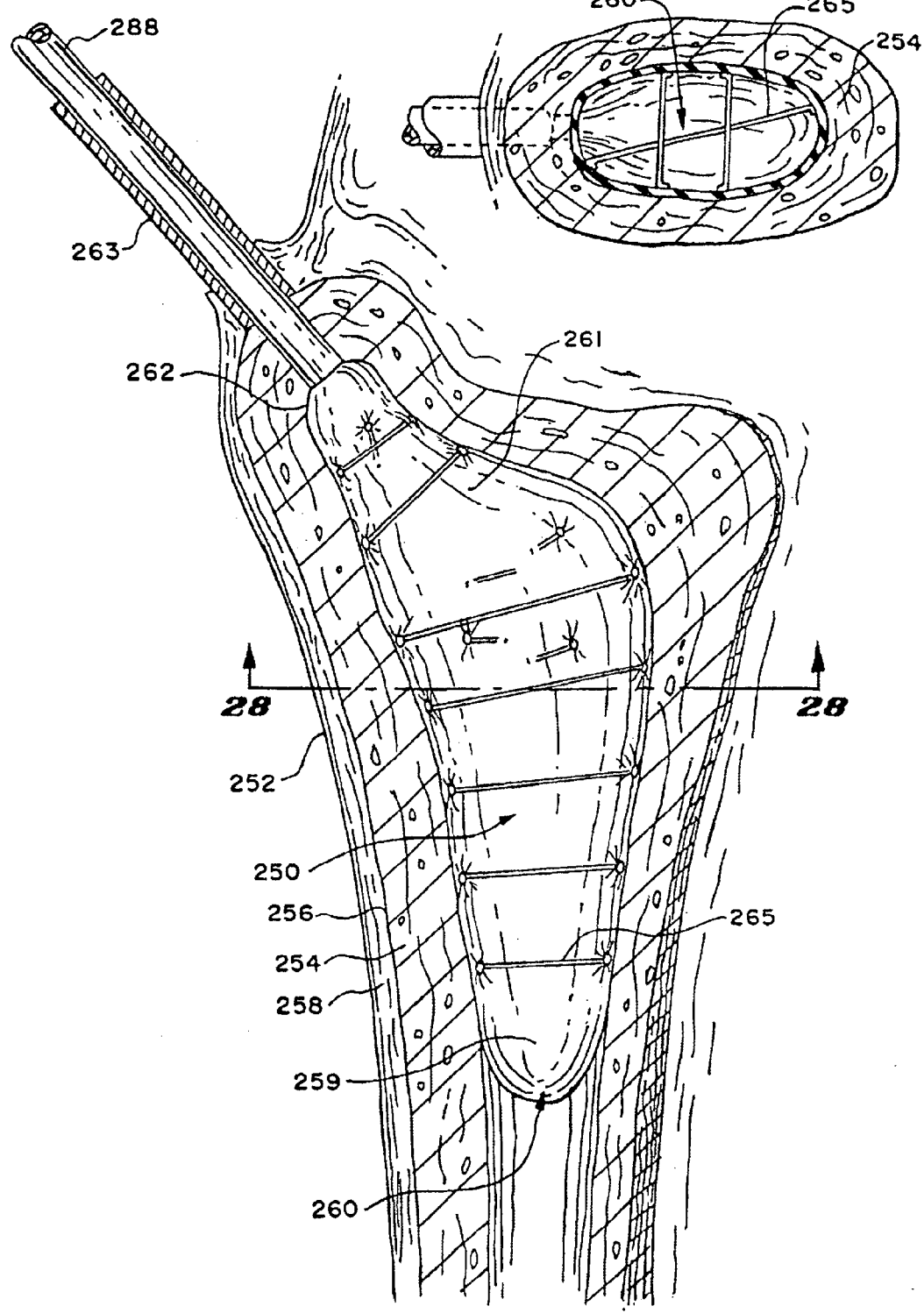
FIG. 27 is a dorsal view of a representative expandable body having a humpback banana-shaped geometry in use in a right distal radius.

FIGS. 27 and 28 show a representative expandable body 260 for use in the distal radius. The body 260, which is shown deployed in the distal radius 252, has a shape which approximates a pyramid but more closely can be considered the shape of a humpbacked banana. The geometry of the body 260 substantially fills the interior of the space of the distal radius to compact cancellous bone 254 against the inner surface 256 of cortical bone 258.

The body 260 has a lower, conical portion 259 which extends downwardly into the hollow space of the distal radius 252. This conical portion 259 increases in cross section as a central distal portion 261 is approached. The cross section of the body 260 is shown at a central location (FIG. 27), which is near the widest location of the body 260. The upper end of the body 260, denoted by the numeral 262, converges to the catheter tube 288 for directing a liquid into the body 260 to expand it and force the cancellous bone against the inner surface of the cortical bone.

The shape of the body 260 is determined and restrained by tufts formed by string restraints 265. These restraints are optional and provide additional strength to the body 260, but are not required to achieve the desired configuration.

The body 260 is placed into and taken out of the distal radius in the same manner as that described above with respect to the vertebral bone.

Typical dimensions of the distal radius body vary as follows:

The proximal end of the body 260(i.e. the part nearest the elbow) is cylindrical in shape and will vary from 0.4×0.4 cm to 1.8×1.8 cm.

The length of the distal radius body will vary from 1.0 cm to 12.0 cm.

The widest medial to lateral dimension of the distal radius body, which occurs at or near the distal radio-ulnar joint, will measure from 0.5 cm to 2.5 cm.

The distal anterior-posterior dimension of the distal radius body will vary from 0.4 to 3.0 cm.

B. Expandable Body for Proximal Humerus Fracture

The selection of an appropriate expandable body 266 to treat a given proximal humeral fracture (Region 606 in FIG. 43) depends on the radiologic size of the proximal humerus and the location of the fracture.

Figure 29A:
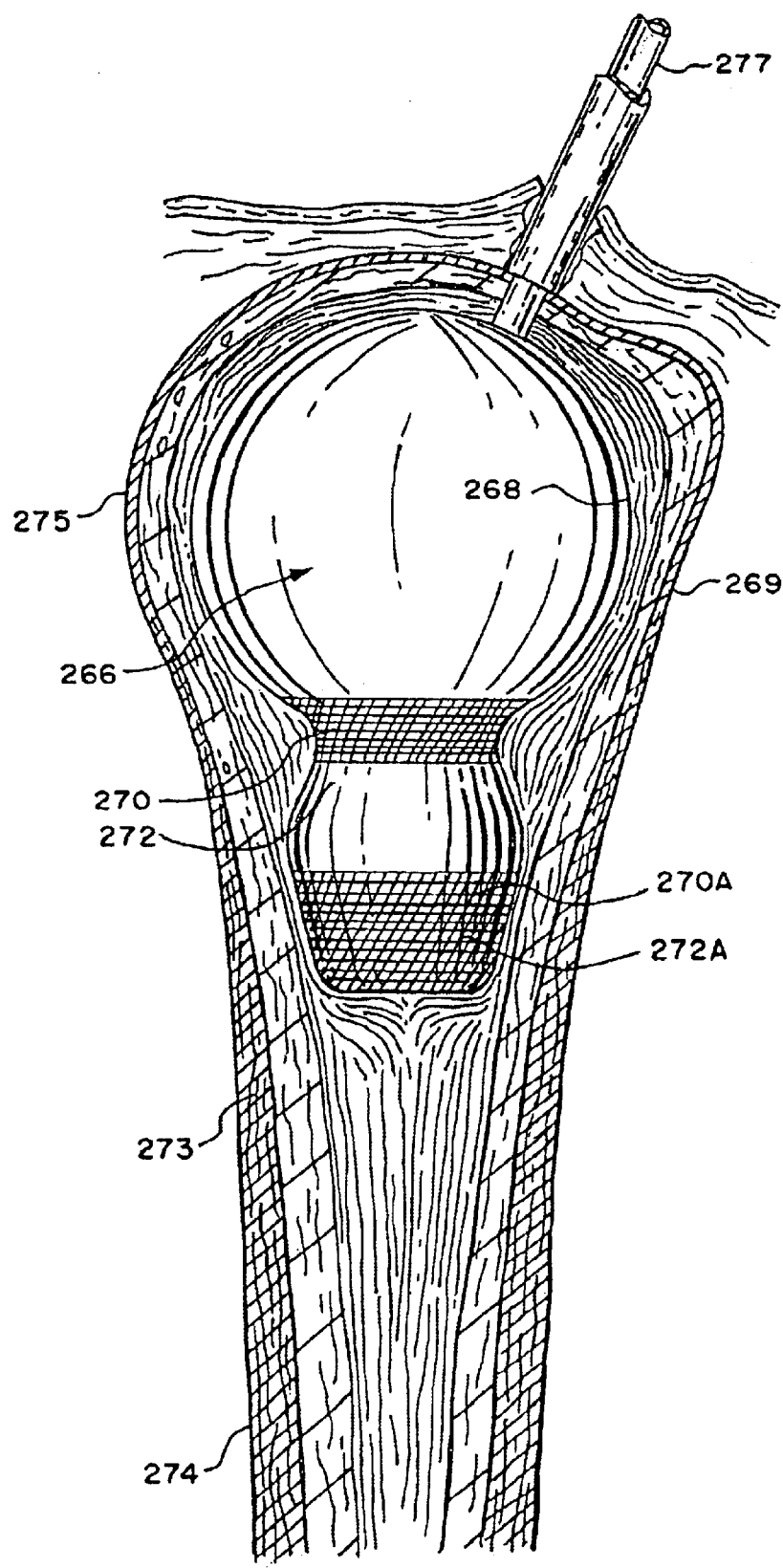
FIG. 29A is a representative expandable body having a spherical shape with a base, located in a proximal humerus and viewed from the front (anterior) of the left proximal humerus.

FIG. 29A shows a representative embodiment of an expandable body 266 for use in the proximal humerus 269. The body 266 is spherical for compacting the cancellous bone 268 in a proximal humerus 269. If surrounding cortical bone has experienced depression fracture, expansion of the body 266 also serves to elevate or move the fractured cortical bone back to or near its anatomic position before fracture.

A mesh 270, embedded or laminated and/or winding, may be used to form a neck 272 on the body 266. A second mesh 270a may be used to conform the bottom of the base 272a to the shape of the inner cortical wall at the start of the shaft. These mesh restraints provide additional strength to the body 266, but the configuration can be achieved through molding of the body.

The body 266 has a catheter tube 277 into which liquid under pressure is forced into the body to expand it to compact the cancellous bone in the proximal humerus. The body 266 is inserted into and taken out of the proximal humerus in the same manner as that described above with respect to the vertebral bone.

Typical dimensions of the expandable body 266 shown in FIG. 29A for proximal humerus fracture vary as follows:

The spherical end of the body will vary from 0.6×0.6 cm to 3.0×3.0 cm.

The neck of the proximal humeral fracture body will vary from 0.5×0.5 cm to 3.0×3.0 cm.

The width of the base portion or distal portion of the proximal numeral fracture body will vary from 0.5×0.5 cm to 2.5×2.5 cm.

The length of the body will vary from 3.0 cm to 14.0 cm.

Figure 29B:
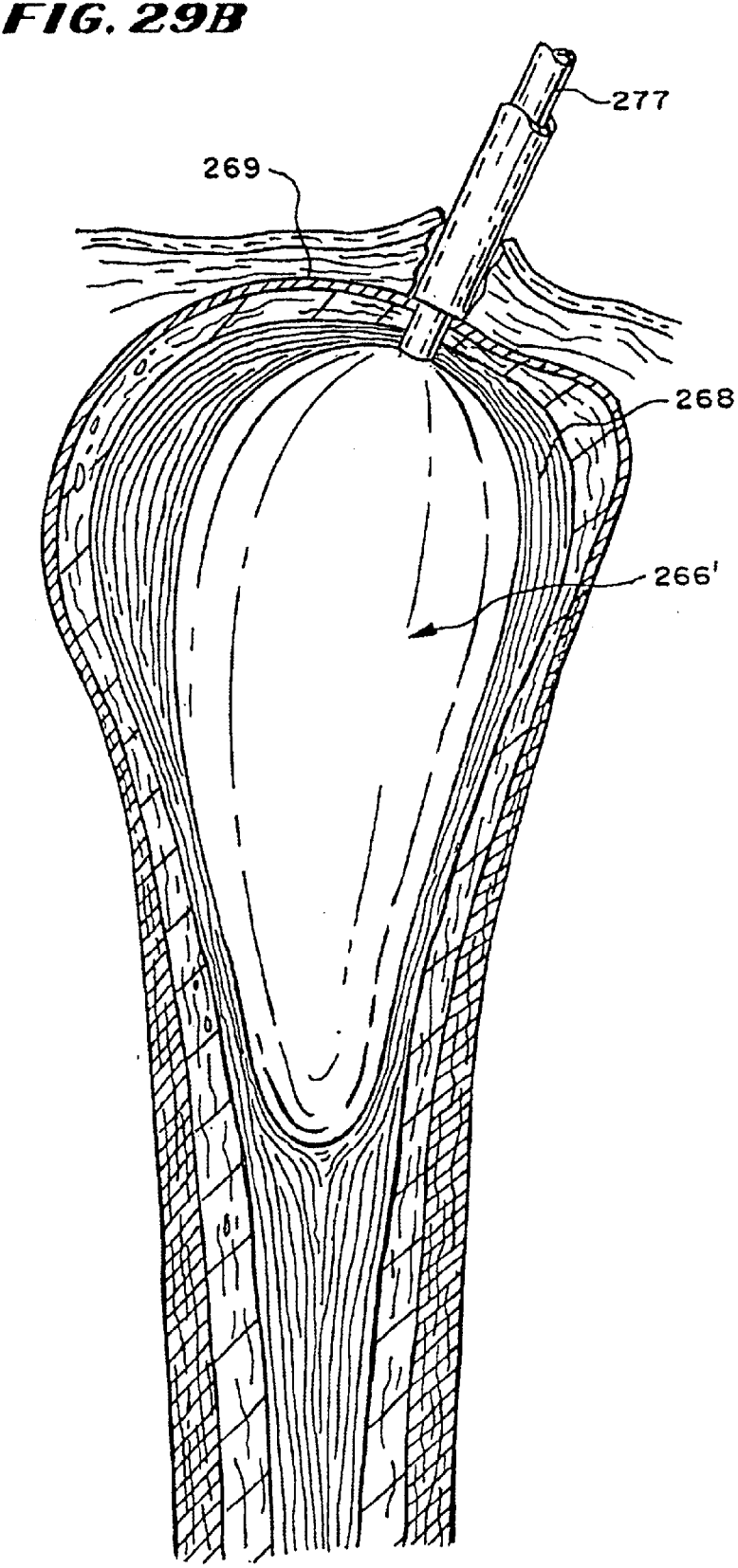
FIG. 29B is a representative expandable body having a cylindrical shape, located in a proximal humerus and viewed from the front (anterior) of the left proximal humerus.

FIG. 29B shows another representative embodiment of an expandable body 266' for use in the proximal humerus 269. Instead of being spherical, the body 266' shown in FIG. 29B has a generally cylindrical geometry for compacting the cancellous bone 268 in a proximal humerus 269. Alternatively, the cylindrical body 266' can be elongated to form an elliptical or football-shaped geometry. Typical dimensions for a cylindrical or elliptical body vary from 0.6 cm to 3.0 cm in diameter to 3.0 cm to 14.0 cm in length.

C. Expandable Body for Proximal Tibial Plateau Fracture

The selection of an expandable body to treat a given tibial plateau fracture (Region 604 in FIG. 43) will depend on the radiological size of the proximal tibial and the location of the fracture.

Figure 30:
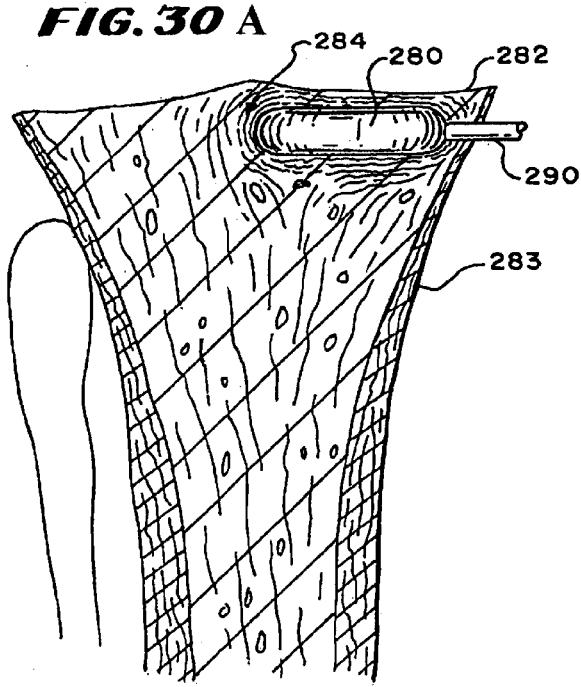
FIG. 30A is a representative embodiment of an expandable body located, as shown in a front (anterior) view of the proximal tibia, introduced beneath the medial tibial plateau.
FIG. 30B is a side elevation view of the expandable body shown in FIG. 30A.
FIG. 30C is a top perspective view of the expandable body shown in FIG. 30A, showing its generally cylindrical geometry.

FIG. 30A shows a representative expandable body 280 for treating a tibial plateau fracture. The body 280 may be introduced into the tibia from any direction, as desired by the physician, for example, from the top, or medial, lateral, anterior, posterior, or oblique approach. In FIG. 30A, the body 280 has been introduced into cancellous bone 284 from the anterior side of the tibia 283 and is shown position in one side 282 of the tibia 283.

The body 280, when substantially inflated (as FIG. 30A shows), compacts the cancellous bone in the layer 284 surrounding the body 280. If the tibia plateau has experienced depression fracture, expansion of the body 280 also serves to move the tibia plateau back to or near its anatomic elevation before fracture, as FIG. 30A shows. Fractures on both the medial and lateral sides of the tibia can be treated in this manner.

Figure 30B:
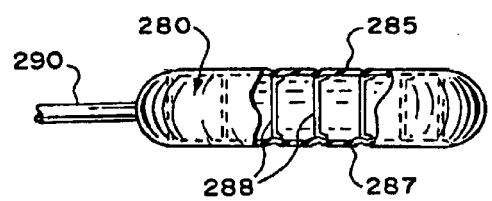
Figure 30C:
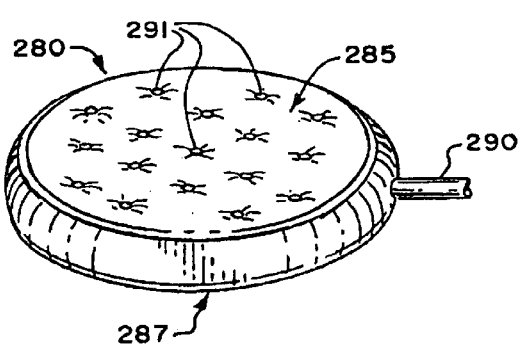

As FIG. 30B shows, the body 280 has a pair of opposed sides 285 and 287. The sides 285 and 287 are interconnected by restraints 288, which pass through the body 280. FIG. 30C shows the tied-off ends 291 of the restraints 288.

The restraints 288 can be in the form of strings or flexible members of any suitable construction. The restraints 288 limit expansion of the body 280 prior to failure. The restraints 288 make the sides 285 and 287, when the body 280 is substantially expanded, substantially parallel with each other and, thereby, non-spherical.

Figure 31:
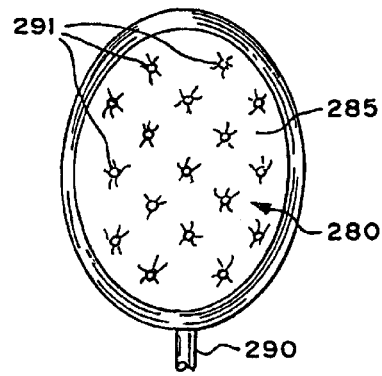
FIG. 31 is a top plan view of another representative embodiment of an expandable body for use in treating tibial plateau fractures, having a generally elliptical geometry.

A tube 290 is coupled to the body 280 to direct liquid into and out of the body to expand it. The body is inserted into and taken out of the tibia in the same manner as that described above with respect to the vertebral bone. FIG. 30C shows a substantially circular configuration for the body 280, although the body 280 can also be substantially elliptical, as FIG. 31 shows.

Figure 32:
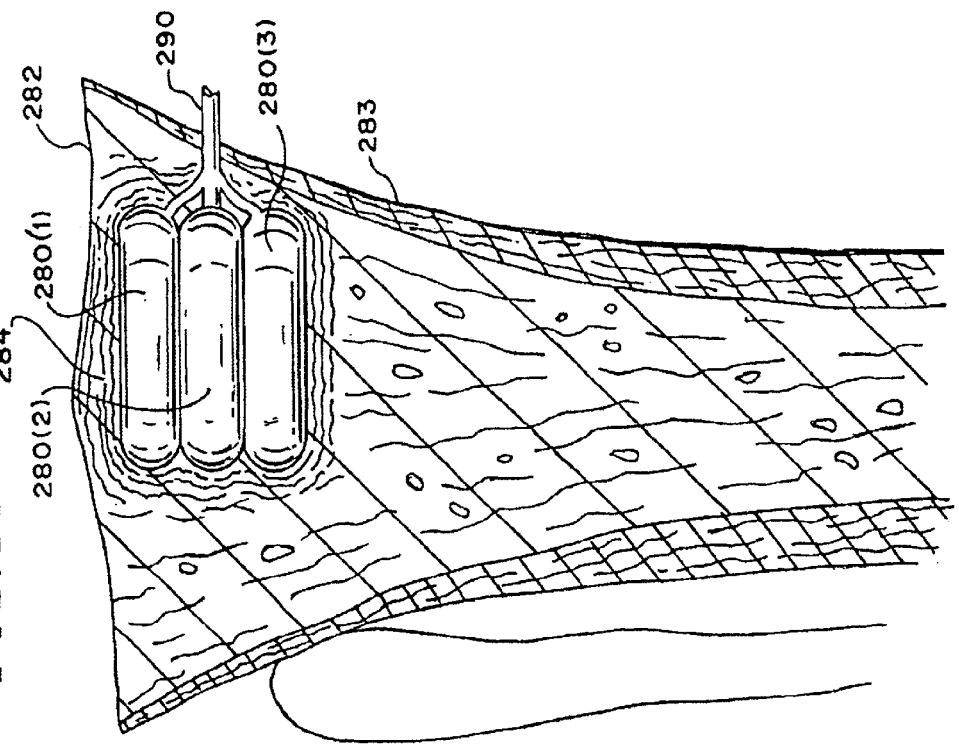
FIG. 32 is a side view of multiple expandable bodies stacked on atop another for use, for example, in treating tibial plateau fractures.

Other geometries and configurations can also be used. For example, as FIG. 32 shows, two or more expandable bodies 280(1), 280(2), and 280(3) can be stacked one atop another to produce a different cavity geometry and to enhance plateau fracture displacement. The multiple bodies 280(1), 280(2), and 280(3) can comprise separate units or be joined together for common deployment. When deployed as separate units, the bodies 280(1), 280(2), and 280(3) can enter through the same access point or from different access points.

Figure 33:
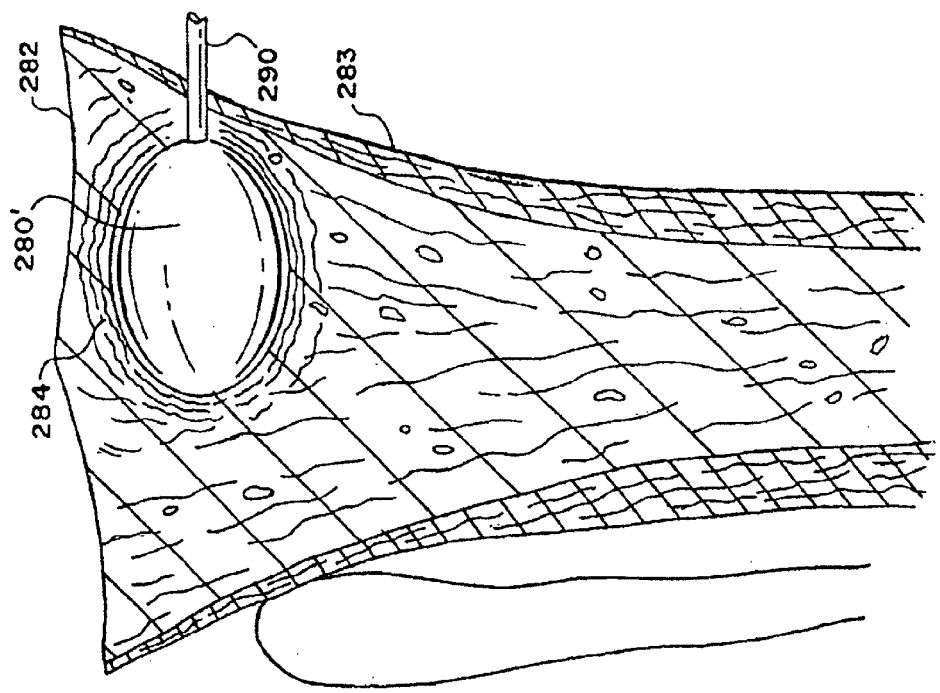
FIG. 33 is another representative embodiment of an expandable body having an egg-shaped geometry located, as shown in a front (anterior) view of the proximal tibia, introduced beneath the medial tibial plateau.

As another example, as FIG. 33 shows, the body 280' can assume an egg shape when substantially inflated, to form a cavity and reshape broken bones. Other geometries, such as cylindrical or spherical, can also be used for the same purpose.

Typical dimensions of the body 280 for treating proximal tibial plateau fracture vary as follows:

The thickness or height of the body will vary from 0.3 cm to 5.0 cm.

The anterior-posterior (front to back) dimension will vary from 1.0 cm to 6.0 cm.

The medial to lateral (side-to-side) dimension will vary from 1.0 cm to 6.0 cm.

Figure 44:
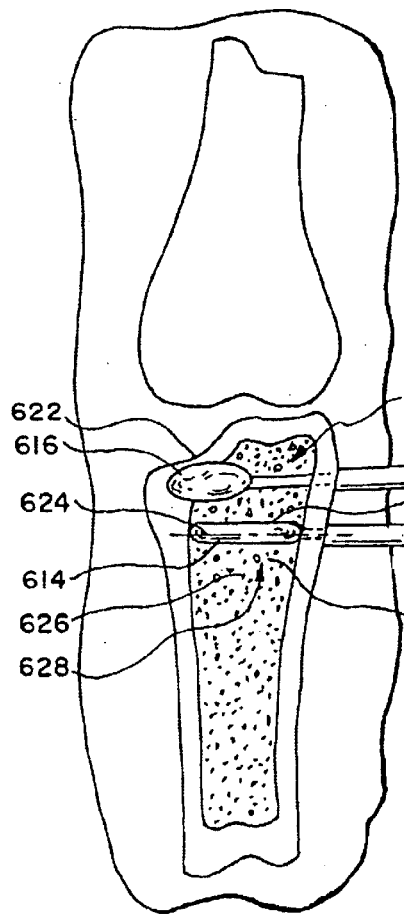
FIG. 44 is a representative embodiment of multiple expandable bodies located, as shown in a front (anterior) view, within the proximal tibia, both introduced beneath the medial tibial plateau, one of the bodies being substantially expanded to form an interior barrier and serve as a platform for the other body, which is shown substantially collapsed.
Figure 45:
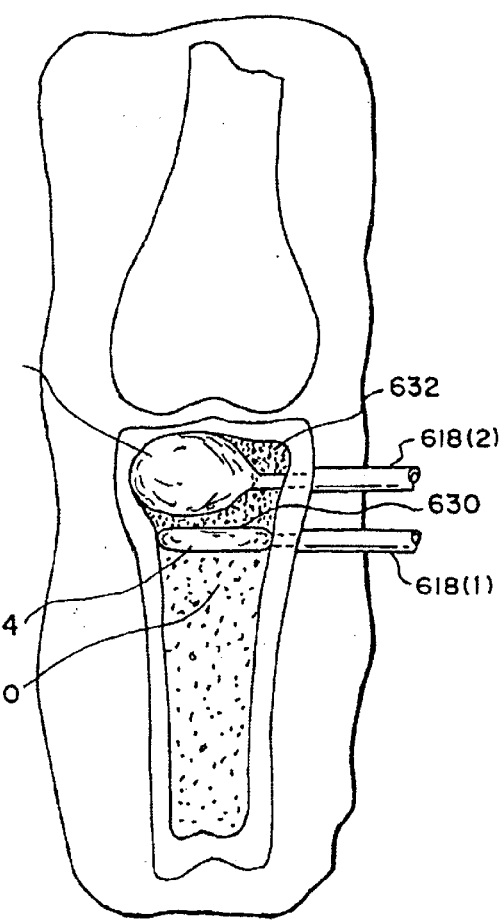
FIG. 45 is a front (anterior) view of the multiple expandable bodies, shown in FIG. 44, with both bodies in substantially expanded conditions to form a cavity within the proximal tibia beneath the medial tibial plateau.

FIGS. 44 and 45 show multiple expandable zones 614 and 616 deployed in cancellous bone 620. One zone 614 serves as a platform to confine and direct the expansion of the other zone 616. For the purpose of illustration, FIGS. 44 and 45 show the multiple zones 614 and 616 used for this purpose to treat a tibial plateau fracture 622.

In the embodiment shown in FIGS. 44 and 45, the zones 614 and 616 comprise separate expandable bodies. It should be appreciated, however, that the zone 614 and 616 can comprise parts of a single expandable body.

In the illustrated embodiment (as FIG. 44 shows), the first expandable body 614 is deployed through a first outer guide sheath 618(1) into cancellous bone 620 below the fracture 622. As FIG. 44 shows, when substantially expanded, the first body 614 expands more along its horizontal axis 624 (i.e., in a side-to-side direction) than along its vertical axis 626 (i.e., in an top-to-bottom direction). The greater expanded side-to-side geometry of the first body 614 compacts cancellous bone in a relatively thin region, which extends substantially across the interior volume 628 occupied by the first body 614. The geometric limits of the body 614 will typically fall just inside the inner cortical walls of the proximal tibia, or whatever bone in which the first body 614 is deployed.

The expanded first body 614 creates a barrier 630 within the interior region 628. Due to the less expanded top-to-bottom geometry of the first body 614, a substantially uncompacted region 632 of cancellous bone is left above the body 614, which extends from the formed barrier 630 upward to the fracture 622. In a representative deployment, the uncompacted region 632 extends about 2 cm below the tibial plateau fracture 622.

As FIG. 44 shows, a second expandable body 616 is deployed through a second outer guide sheath 618(2) into the uncompacted region 632 left between the first body 614, when substantially expanded, and the targeted tibial plateau fracture 622.

Figure 46:
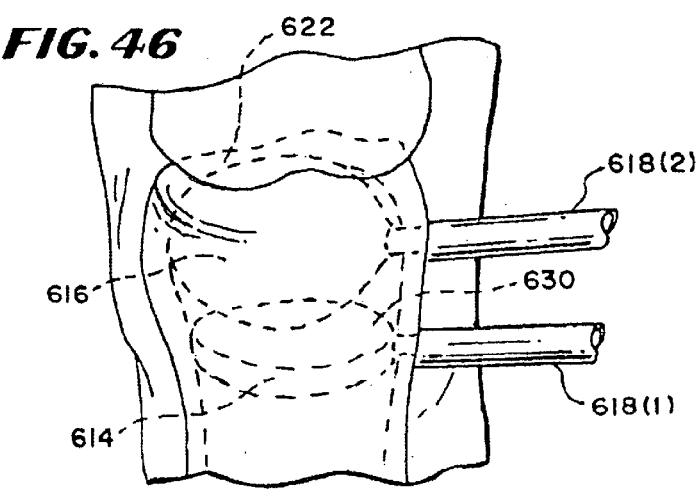
FIG. 46 is an enlarged front (anterior) perspective view of the multiple expandable bodies shown in FIG. 45, with the lower expandable body serving as a platform for the upper expandable body.

As FIG. 45 shows, the second expandable body 616 has a geometry, substantially like that shown in FIGS. 30A to 30C. When substantially inflated, the second body 616 compacts a large percentage of the cancellous bone in the region 632 above the first expandable body 614. The presence of the barrier 630, which the expanded first body 614 creates (see FIG. 46 also), prevents expansion of the second body 616 in a direction away from the tibial platform fracture 622. Instead, the barrier 630 directs expansion of the second body 616 toward the fracture 622. Buttressed by the barrier 630, the expansion of the body 616 is directed against the fractured plateau 622, restoring it to its normal anatomic position, as FIGS. 45 and 46 show.

It should be appreciated that one or more expandable bodies can be used as platforms or barriers to direct the expansion of one or more other expandable bodies in other localized interior bone regions. The barrier makes possible localized cavity formation in interior bone regions. Use of the barrier preserves healthy regions of cancellous bone, while directing the main compacting body toward localized fractures or localized regions of diseased cancellous bone.

D. Expandable Body for Femoral Head

The size of an expandable body for use in the femoral head (Region 608 in FIG. 43) is chosen based upon the radiological or CT scan size of the head of the femur and the location and size of the avascular necrotic bone.

Figure 34:
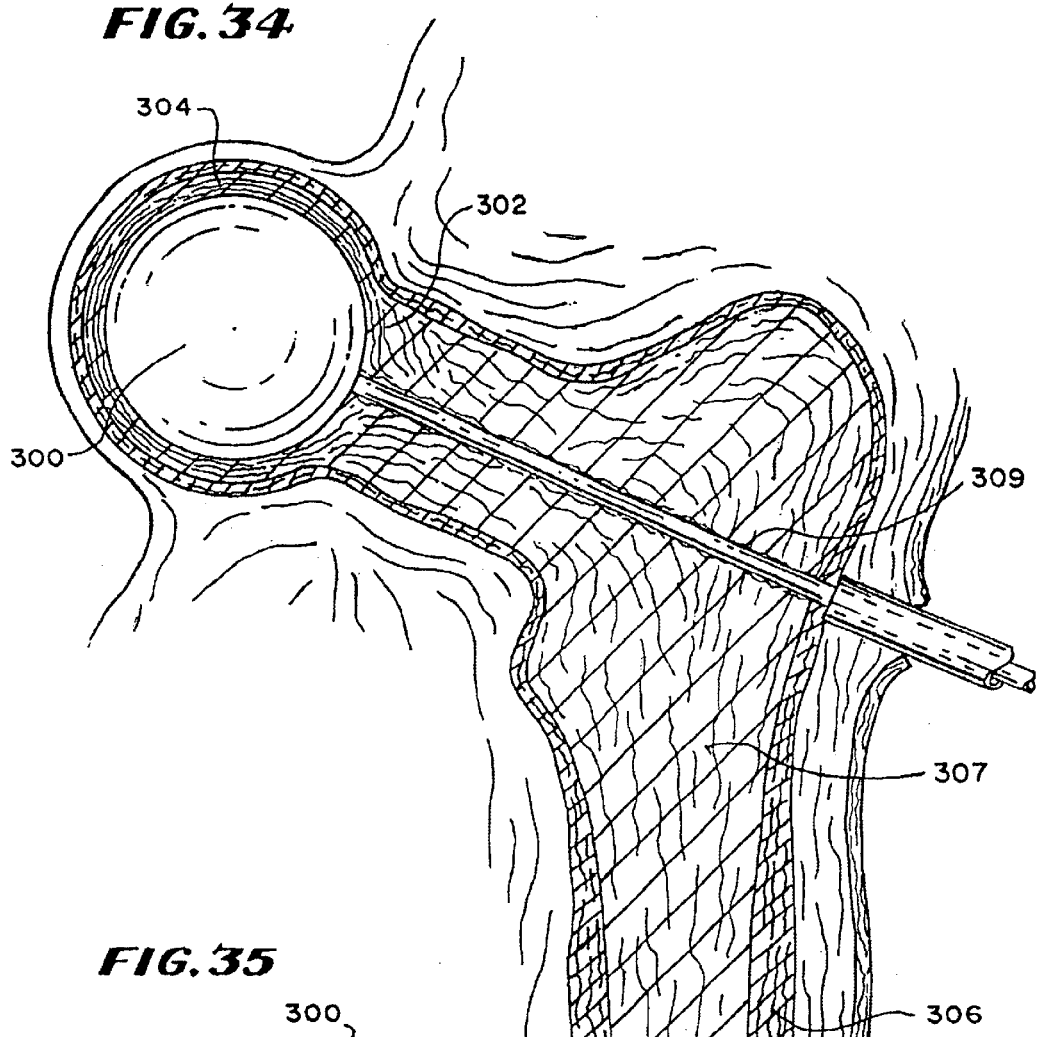
FIG. 34 is a representative embodiment of an expandable body having a spherical-shaped geometry for treating avascular necrosis of the head of the femur (or humerus), which is shown from the front (anterior) of the left hip.

FIG. 34 shows a representative embodiment of an expandable body 300 introduced inside the cortical bone 302 of the femoral head. As FIG. 34 shows, the femoral head is thin at the outer end 304 of the femur and increases in thickness at the lower end 306 of the femur. A tube 309 directs liquid to expand the body 300. The tube 309 extends along the femoral neck and into the femoral head. The expandable body 300 compacts the cancellous bone 307 in this bone region, while also moving fractured cortical bone back to or near its normal anatomic position.

Figure 35:
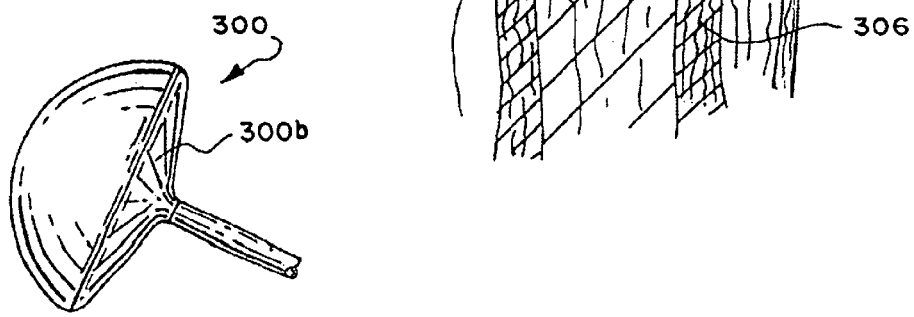
FIG. 35 is a side view of another representative embodiment of an expandable body having a hemispherically-shaped geometry for treating avascular necrosis of the head of the femur (or humerus)

The femoral head is generally spherical in configuration, and the body 300 can have either a hemispherical (see FIG. 35) as well as spherical geometry (as FIG. 34 shows). The hemispherical shape is maintained in FIG. 34 by bonding overlapping portions of the body 300, creating pleats 300b.

The body 300 is inserted into and taken out of the femoral head in the same manner as that described with respect to the vertebral bone.

Typical dimensions of an expandable body for use in treating the femoral head vary as follows:

The diameter of the expandable body will vary from 0.5 cm to up to 4.5 cm. The dimensions of the hemispherical body (FIG. 35) are the same as the those of the spherical body (FIG. 34), except that approximately one half is provided.

E. Expandable Body for Prevention of Hip Fracture

Patients with bone density in the hip (Region 612 in FIG. 43) below a threshold value are at increased risk of hip fracture, and lower densities create greater risk. Patient selection is done through a bone density scan.

Figure 36A:
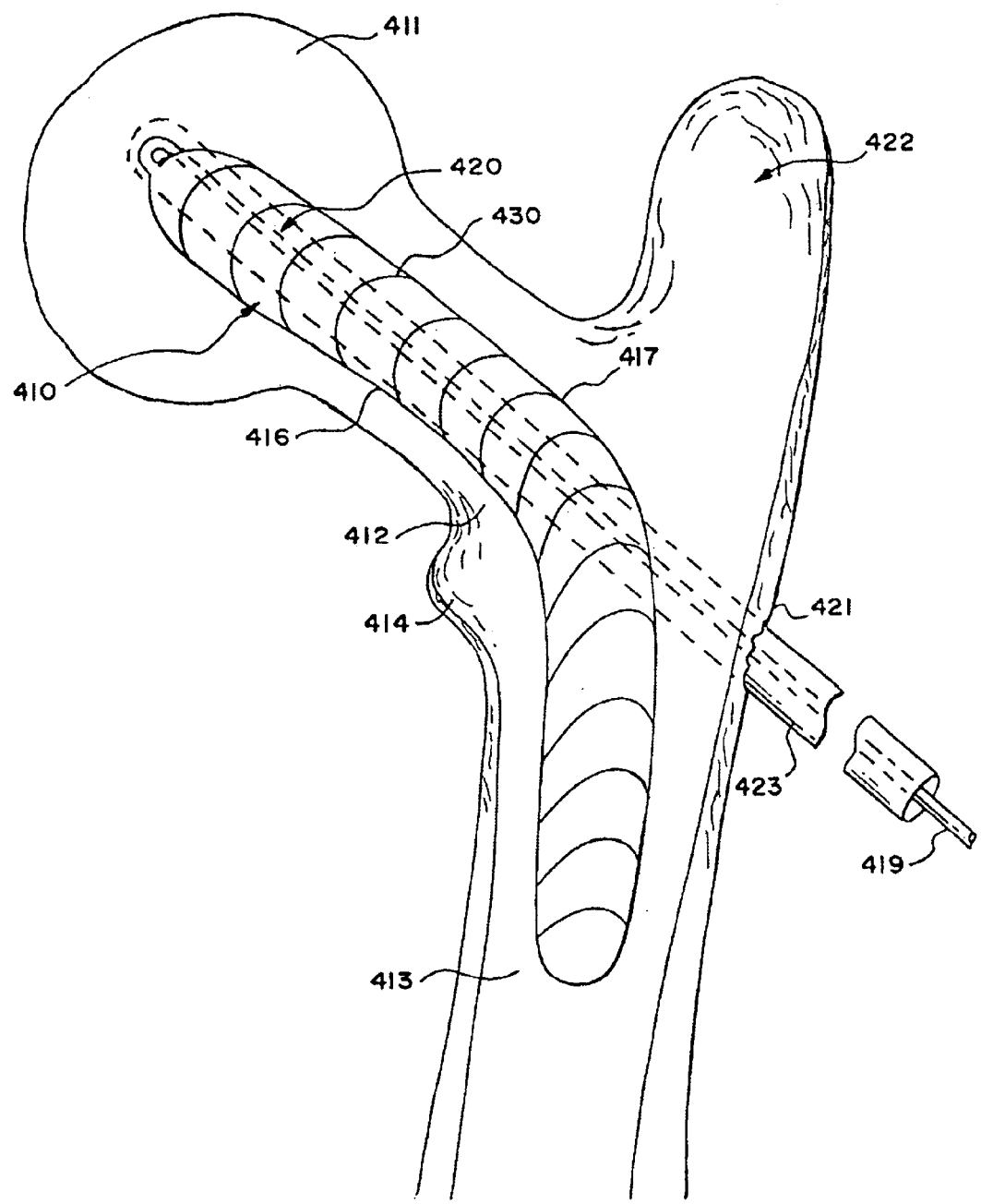
FIG. 36A is a view of a representative expandable body having a bent-geometry for preventing hip fracture, as seen from the front (anterior) of the left hip.

FIG. 36A shows a representative embodiment of an expandable body 410 having a "boomerang" geometry for use in preventing hip fracture. When substantially expanded (as FIG. 36A shows), the body 410 forms a cylinder, which gradually bends in the middle, like a boomerang, and extends from about 0.5 cm from the end of the femoral head 411 through the femoral neck 412 and down into the proximal femoral diaphysis 413 about 5 to 7 cm past the lesser trochanter 414.

Expansion of the body 410 is limited to achieve the described geometry by rings 430 of inelastic material. The rings 430 are held in a spaced apart relationship along one side of the body 410 by attachment to an inelastic band 416, which runs the length of that side of body 410. The rings 430 are held in a farther spaced apart relationship along the opposite side of the body 410 by attachment to another, longer inelastic band 417, which runs the length of the opposite side of the body 410. A tube 419 conveys liquid to inflate the body 410.

Prior to deployment within the body, the body 410 is collapsed and rolled up and held against the inflation tube 419 using, for example, with frangible connectors that will break as the body is subject to expansion. To deploy the body 410 into the hip, the surgeon uses a power drill under radiographic guidance to create a cavity 420, which is, for example, about 4 to 6 mm wide starting at the lateral femoral cortex 421 and proceeding into the femoral head 411. The body 410 is deployed through a guide sheath 423, following the cavity 420. The body 410 is deployed, prior to expansion, facing the lesser trochanter 414, so that expansion occurs toward the femoral diaphysis 413, and not toward the greater trochanteric region 422.

The expansion of the body 410 is guided by the rings 430 and bands 416 and 417, which cause bending of the body 410 downward into the lesser trochanter 414. Optionally, a second cavity can be drilled down into the diaphysis 413, starting from the same entry point or from the other side.

The body length is chosen by the physician to extend about 0.5 cm from the end of the femoral head, through the femoral neck and into the proximal femoral diaphysis, usually about 4 to 8 cm below the lesser trochanter. The body diameter is chosen by measuring the inner cortical diameter of the femoral neck (the most narrow area) and subtracting 0.5 cm. The preferred dimensions of the body 410 are a total length of 10–20 cm and a diameter of about 1.0–2.5 cm.

Patients having the lowest bone densities in the femoral head may require greater compacting in the femoral head, which may, for example, be provided by using two bodies, one after the other: the bent body 410 followed by the femoral head body (inserted at the same point and expanded prior to inserting any supporting material). Alternatively, the bent body 410 may be adapted to have a distal portion that approximates the shape of the femoral head body.

Figure 36B:
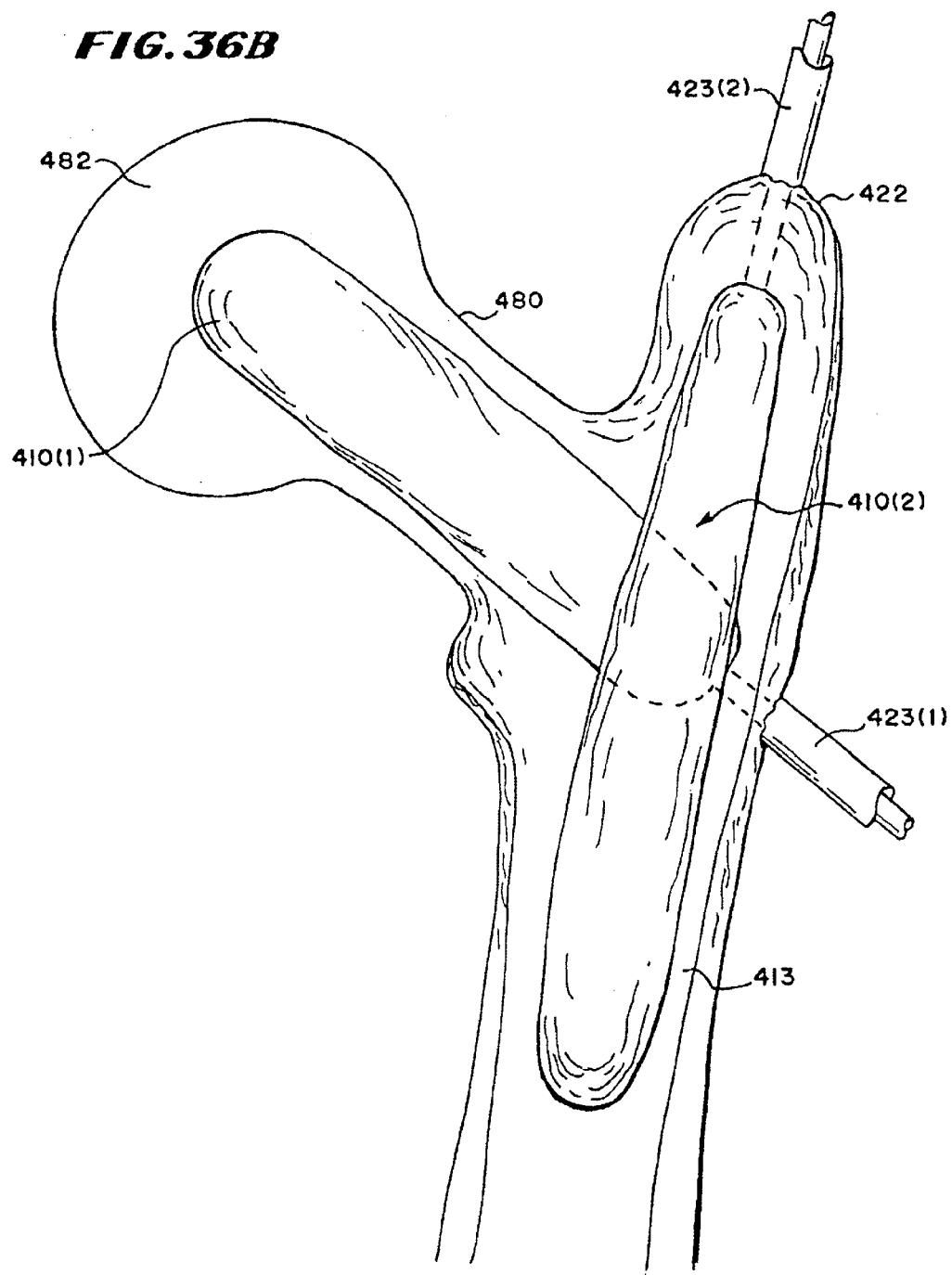
FIG. 36B is a view of multiple expandable bodies individually deployed through multiple access points into the left hip for preventing hip fracture.

The geometry of the single, restrained body 410 can be approximated by multiple expandable bodies deployed separately, or coupled together, or stacked together. FIG. 36B shows a representative embodiment of the use of multiple expandable bodies in the hip region.

As FIG. 36B shows, a first expandable body 410(1) is introduced through a first outer guide sheath 423(1) in the proximal lateral cortex of the femoral shaft. The first body 419(1) is deployed across the femoral neck 480 into the femoral head 482.

A second expandable body 410(2) is introduced through a second outer guide sheath 423(2) in the greater trochanter 422 of the femur. The first body 419(1) is deployed in the direction of the femoral diaphysis 413.

Other approaches can be used. For example, one body can be introduced through the femoral neck 480, and the other body can be introduced along the shaft of the femur.

One or both of the bodies 410(1) and 410(2) can include external restraints to limit expansion, in the manner described with regard to the body 410. Expansion of the bodies 410(1) and 410(2) compacts cancellous bone to form a cavity having a geometry approximating that formed by the single body 410.

F. Expandable Body for Calcaneus Fracture

The size of an expandable body for use in treating fracture of the calcaneus (heel bone) (Region 610 in FIG. 43) is chosen based upon the radiological or CT scan size of the calcaneus and the location and size of the fracture.

Figure 37A:
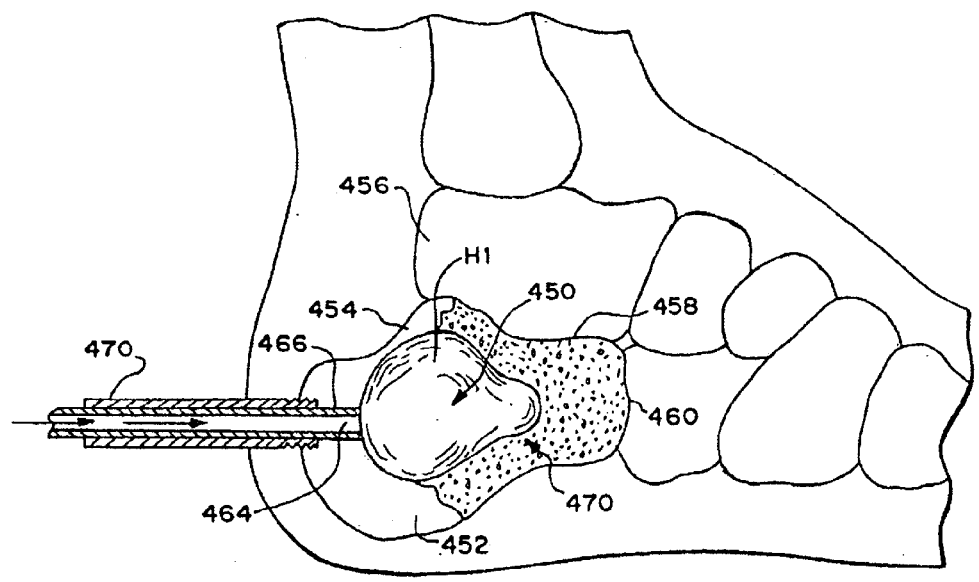
FIG. 37A is a view of a representative expandable body having an asymmetric bow tie-shape for use in treating fracture of the calcaneus bone, shown in lateral view within the calcaneus.
Figure 37B:
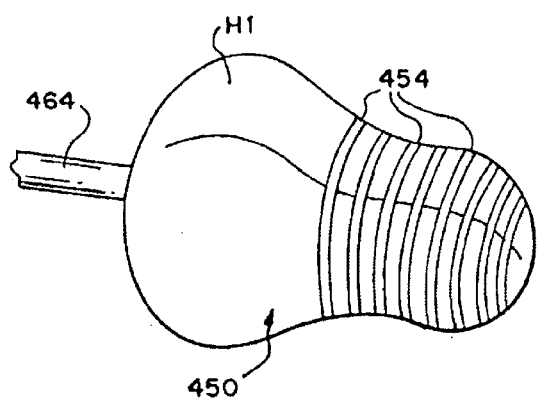
FIG. 37B is a perspective top view of the expandable body shown in FIG. 37A when substantially expanded outside the calcaneus.

FIGS. 37A and 37B show a representative expandable body 450 for treating fracture of the calcaneus 452. A tube 464 conveys liquid into the body 450 to expand it.

In FIG. 37A, the body 450 is deploy into the calcaneus 452 by a posterior approach, through the tuberosity. Other approaches can be used, as desired by the physician. A power drill opens a passage 466 through the tuberosity into the calcaneus. An outer guide sheath 470 is positioned within the passage 466, abutting the posterior of the calcaneus, in the manner previously described in obtaining access to a vertebral body. The body 450 is introduced through the guide sheath 470 and formed passage 466 into the calcaneus.

Expansion of the body 450 is limited within the confines of the calcaneus by inelastic peripheral bands 454 (see FIG. 37B). The bands 454 constrain expansion of the body 450 to an asymmetric, pear-shaped geometry, best shown in FIG. 37B. The pear-shaped geometry has a major dimension H1 occupying the region of the posterior facet 454. The major dimension H1 is located here, because the part of the calcaneus most likely to require elevation and realignment during expansion of the body 450 is the depressed part of the posterior facet 454 of the calcaneus, where the posterior facet 454 abuts the talus 456.

The pear-shaped geometry has a smaller, minor dimension occupying the region of the anterior facet 458 of the calcaneus, near the calcaneal-cuboid joint 460, between the calcaneus and cuboid bone 462.

Expansion of the body 410 compacts cancellous bone 470 within the calcaneus 452. The expansion also lifts a depression fracture of the posterior facet 454 back to or near its original anatomic elevation adjacent the talus 456. When collapsed and removed, the body 410 leaves a cavity in cancellous bone into which filling material can be introduced in the manner previously described.

Figure 38:
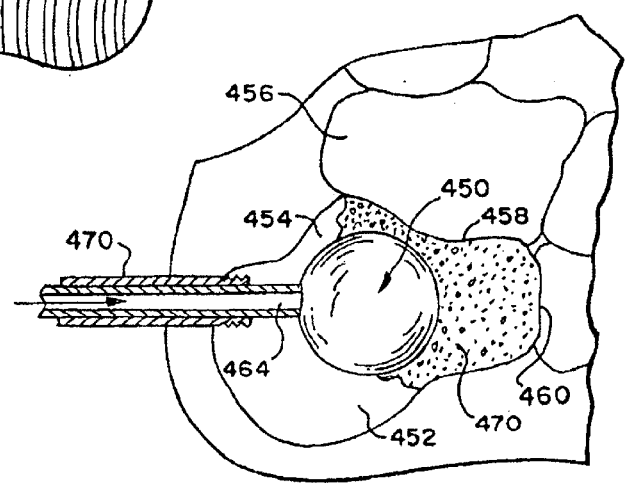
FIG. 38 shows a representative embodiment of an expandable body having a spherical or egg-shaped geometry shown in lateral view deployed within the calcaneus.

FIG. 38 shows another representative embodiment of an expandable body 450' for use in treating fractures in the calcaneus. The body 450' in FIG. 38 has a more spherical or egg-shaped geometry than the pear-shaped body 450 shown in FIG. 37B. Like the pear-shaped body 450, the body 450', when expanded within the calcaneus, forms a cavity within cancellous bone and realigns fractured cortical bone at or near its normal anatomic position.

III. Selection of Other Expandable Bodies (Further Overview)

Different sizes and/or shapes of expandable bodies may be used at sites not specified above, such as the jaw bones, the midshaft of the arm and leg bones, the cervical vertebral bodies, the foot and ankle bones, the pelvis, the ribs, and the like.

The choice of the shape and size of a expandable body takes into account the morphology and geometry of the site to be treated. As before stated, the shape of the cancellous bone to be compressed, and the local structures that could be harmed if bone were moved inappropriately, are generally understood by medical professionals using textbooks of human skeletal anatomy along with their knowledge of the site and its disease or injury. Precise dimensions for a given patient can be further determined by X-ray of the site to be treated.

As one general guideline, the selection of the geometry of the expandable body should take into account that at least 40% of the cancellous bone volume needs to be compacted in cases where the bone disease causing fracture (or the risk of fracture) is the loss of cancellous bone mass (as in osteoporosis). The preferred range is about 30% to 90% of the cancellous bone volume. Compacting less of the cancellous bone volume can leave too much of the diseased cancellous bone at the treated site. The diseased cancellous bone remains weak and can later collapse, causing fracture, despite treatment.

Another general guideline for the selection of the geometry of the expandable body is the amount that the targeted fractured bone region has been displaced or depressed. The expansion of the body within the cancellous bone region inside a bone can elevate or push the fractured cortical wall back to or near its anatomic position occupied before fracture occurred.

However, there are times when a lesser amount of cancellous bone compaction is indicated. For example, when the bone disease being treated is localized, such as in avascular necrosis, or where local loss of blood supply is killing bone in a limited area, the expandable body can compact a smaller volume. This is because the diseased area requiring treatment is smaller.

Another exception lies in the use of an expandable body to improve insertion of solid materials in defined shapes, like hydroxyapatite and components in total joint replacement. In these cases, the body shape and size is defined by the shape and size of the material being inserted.

Yet another exception is the delivery of therapeutic substances, which will be described in greater detail later. In this case, the cancellous bone may or may not be diseased or adversely affected. Healthy cancellous bone can be sacrificed by significant compaction to improve the delivery of a drug or growth factor which has an important therapeutic purpose. In this application, the size of the expandable body is chosen by the desired amount of therapeutic substance sought to be delivered. In this case, the bone with the drug inside is supported while the drug works, and the bone heals through exterior casting or current interior or exterior fixation devices.

Generally speaking, providing relatively inelastic properties for the expandable body, while not always required, is nevertheless preferred when maintaining a desired shape and size within the bone is important, for example, in bone graft placement or in a vertebral body, where the spinal cord is nearby. Using relatively inelastic bodies, the shape and size can be better predefined, taking into account the normal dimensions of the outside edge of the cancellous bone. Use of relatively inelastic materials also more readily permits the application of pressures equally in all directions to compress cancellous bone. Still, substantially equivalent results can usually be achieved by the use of multiple expandable bodies having highly elastic properties, if expansion is controlled by either internal or external restraints, as previously disclosed.

IV. Confinement of Filling Material

A. Dual Stage Filling

FIGS. 39A to 39D show a multiple stage process for introducing filling material into a cavity formed by an expandable body in cancellous bone. The process is shown in association with treating a vertebral body. This is for the purpose of illustration. It should be appreciated that the process can be used in the treatment of all bone types.

Figure 39B:
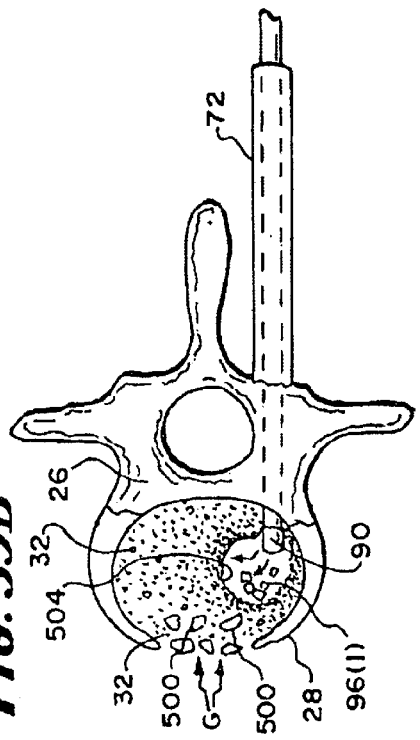
FIGS. 39A to 39D show a multiple stage process of introducing filling material into a cavity formed by an expandable body in cancellous bone, to prevent or impede flow or seepage of filling material from the interior of the bone.
Figure 39D:
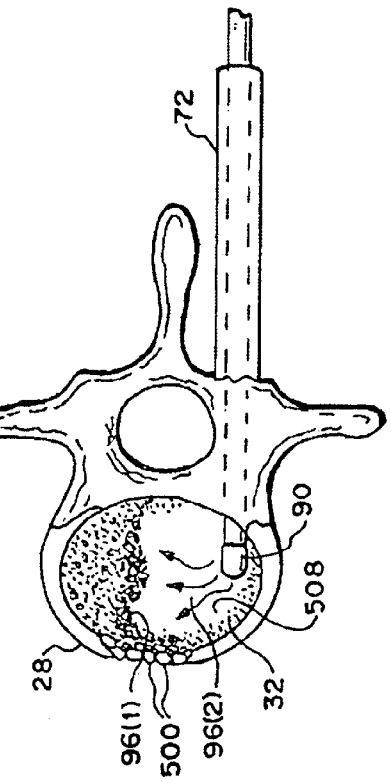
Figure 39A:
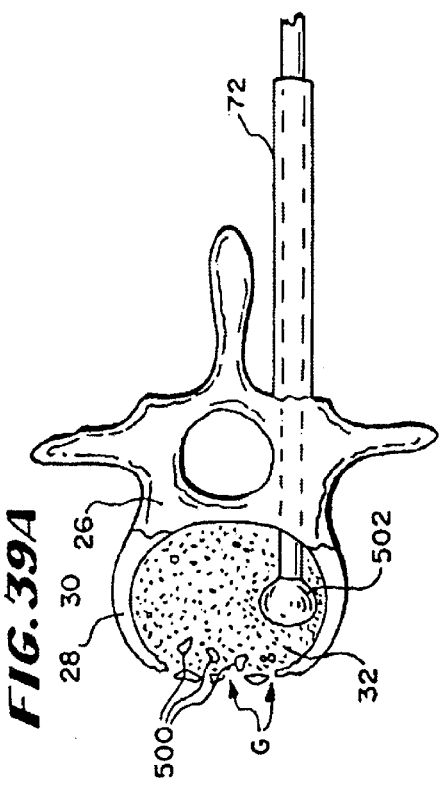

Use of the multi-stage process is indicated when pre-examination of the targeted bone reveals that a portion of the cortical wall 28 has fractured or failed (as FIG. 39A shows at the anterior region of the vertebral body 26). The failed cortical wall 28 creates gaps and cracks (designated G in FIG. 39A). Typically, remnant chips 500 of the failed cortical bone 28 may lay in the cancellous bone 32 in the region where cortical wall failure has occurred. Filling material can flow or seep through these gaps or cracks C outside of the interior volume of the bone.

The process begins at the point where the outer guide sheath 72 has been positioned and the guide pin removed in the manner previously described. The physician introduces a first expandable body 502 into the cancellous bone 32 near the failed cortical bone region, as FIG. 39A shows. The first expandable body 502 is sized, when substantially expanded, to occupy a relatively small volume (i.e., less than about 20%) of the volume of cancellous bone 32 in interior volume 30.

The physician expands the first expandable body 502, compacting a relatively small region of cancellous bone. Upon collapse and removal of the first body 502, a small cavity 504, caused by the compaction, remains (as FIG. 39B shows).

The physician introduces the injector tip 90 and injects an aliquot of filling material 96(1) (for example, about 1 cc to about 9 cc) into the formed small cavity 504 (as FIG. 39B shows).

Figure 39C:
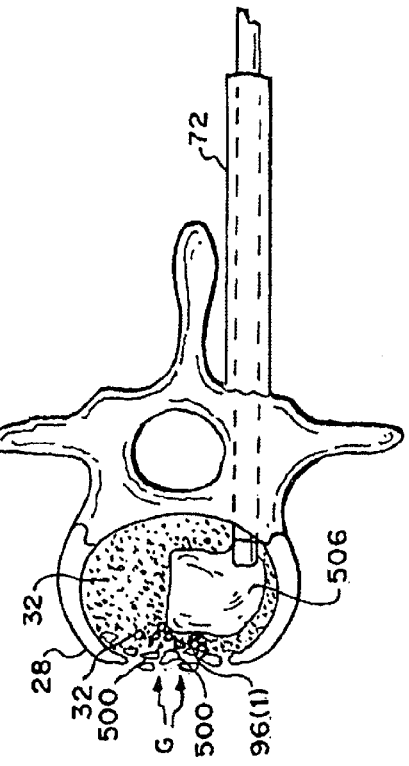

In a short time interval (before the filling material 96(1) is allowed to substantially set and harden), the physician withdraws the injector tip 90 and introduces a second expandable body 506 into the cancellous bone 32 (see FIG. 39C). The second expandable body 506 is larger than the first body 502. The second body 506 is sized to create the desired geometry for the therapeutic main cavity 508 in cancellous bone 32.

As FIG. 39C shows, expansion of the second body 506 displaces the earlier injected aliquot of filling material 96(1) in the cavity 504 toward the failed cortical wall region. The aliquot of filling material 96(1) will envelop remnant chips 500 of cortical bone lying in its path. The material 96(1) and enveloped chips 500 are pressed against the failed cortical bone region as expansion of the second body 506 progresses. The first aliquot of filling material 96(1) will begin to set and harden as the main therapeutic cavity 508 is being formed by the expansion of the second body 506. The second body 506 is collapsed and removed, leaving the main cavity 508.

As FIG. 39D shows, the first aliquot of filling material 96(1) provides a viscous or (in time) hardened boarder region along the anterior edge of the cavity 508. As subsequent injection of additional filling material 96(2) into the main cavity 508 proceeds, as FIG. 39D shows, the viscous or hardened boarder region 96(1) impedes passage of the additional filling material 96(2) as it fills the main cavity 508. The viscous or hardened boarder region 96(1) serves as a dam, keeping the additional filling material 96(2) entering the main cavity 508 from seeping from the vertebral body 26.

B. Interior Mesh

Figure 41:
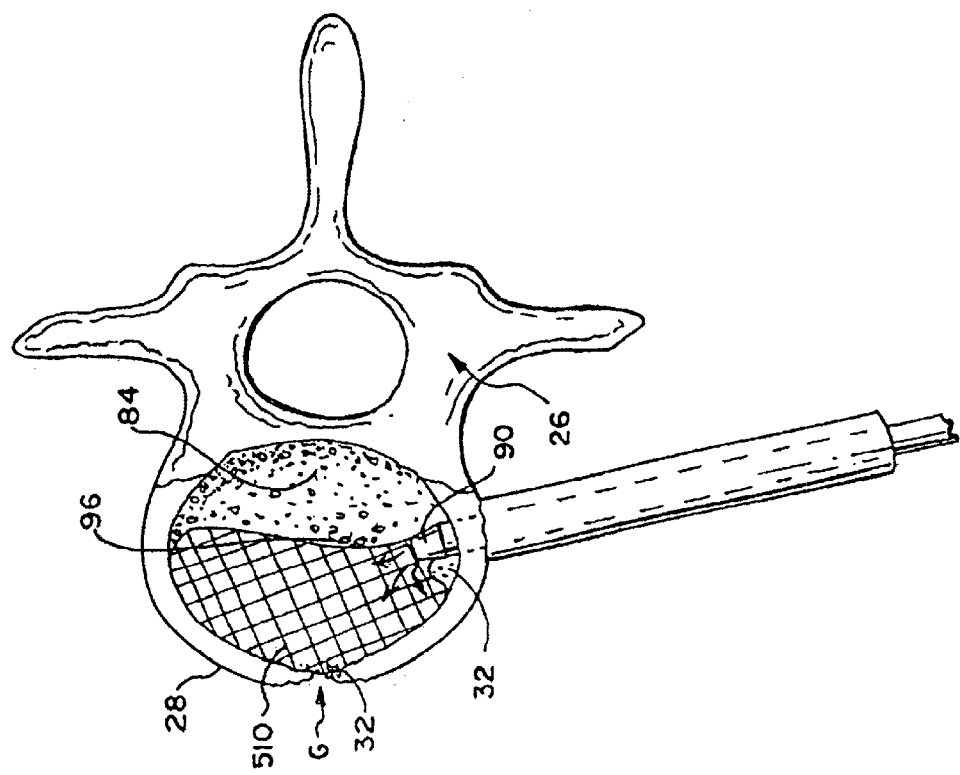
FIG. 41 is a coronal view of a vertebra, with parts broken away and in section, showing the deployment of the mesh shown in FIG. 40 within the vertebral body.
Figure 40:
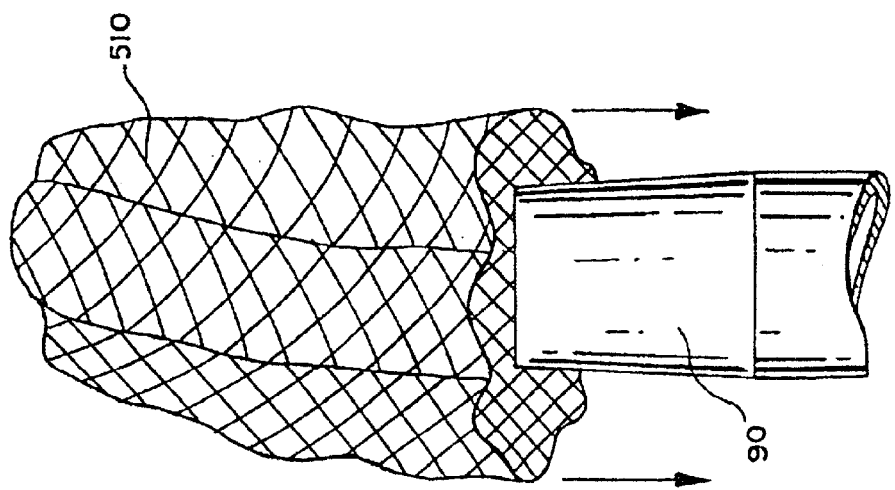
FIG. 40 is an elevation view of an injector tip for filling material, over which a mesh is draped, which, when deployed in a cavity formed by an expandable body, impedes or prevents seepage of the material from the cavity.

FIGS. 40 and 41 show the use of an interior mesh 510 in association with the introduction of filling material into a cavity formed by an expandable body in cancellous bone. The mesh 510 is shown in association with treating a vertebral body, but it should be appreciated that the process can be used in the treatment of all bone types.

Use of the mesh 510 is indicated when pre-examination of the targeted bone reveals a failed cortical bone region (as FIG. 41 shows at the anterior region of the vertebral body 26), coupled with the lack of enough bone matter, due to advanced disease or a complex fracture, to adequately fill the failed cortical bone region by compacting using an expandable body. Flowable cement material can flow or seep through the unfilled gaps or cracks (designated G in FIG. 41) present in the failed cortical bone region.

The mesh 510 comprises a woven structure made from biocompatible material like Goretex™ material, Nitinol™ material, or Dacron™ material. The mesh presents a surface area, which is about ⅓rd to ½ of the interior area of the main therapeutic cavity 84 formed by the selected expandable body.

Before deploying the injector tip 90 into the formed cavity 84 (which is deployed in FIG. 41 by posterolateral access), the physician drapes the mesh 510 over the tip 90, as FIG. 40 shows. As FIG. 41 shows, the viscous flow of filling material 96 injected from the tip 90 carries the mesh 510 into the cavity 84 in advance of the filling material 96. The mesh 510 is urged by the filling material 96 into contact with the anterior region of the bone, including the failed cortical bone region. The mesh 510, permeated with viscous material 96 and resting over the failed cortical bone region, impedes passage of filling material, until hardening occurs.

V. Delivery of Therapeutic Materials

A cavity created in cancellous bone by any of the expandable bodies described above can be filled with a medically-appropriate formulation of a drug or a growth factor.

An expandable body can compact infected cancellous bone to create a space which can be filled with the antibiotic gel in an open or minimally invasive procedure. The cavity places and holds the required amount of drug right at the site needing treatment, and protects the drug from being washed away by blood or other fluids.

Not only can the dose be optimized, but additional doses can be applied at later times without open surgery, enhancing the therapeutic outcome. If the required cavity for the optimal drug dose weakens the bone, the bone can be protected from future fracture with a cast or with current internal or external metal or plastic fixation devices.

The therapeutic substance put into bone may act outside the bone as well. A formulation containing chemotherapeutic agent could be used to treat local solid tumors, localized multiple myeloma or even a nearby osteosarcoma or other tumor near that bone.

The cavity formed by an expandable body can be filled with an appropriate supporting material, like acrylic bone cement or biocompatible bone substitute, which carries a therapeutic substance. Alternatively, the therapeutic substance can be separately delivered before injection of the filling material. Thus, using an expandable body, the physician is able to treat a fracture while also delivering a desired therapeutic substance (like an antibiotic, bone growth facer or osteoporosis drug) to the site.

As an alternative, to deliver therapeutic substances, bodies can be dipped in a medical formulation (often a dry powder, liquid or gel)containing a medically-effective amount of any desired antibiotic, bone growth factor or other therapeutic agent to coat the body with the above-mentioned substance before it is inserted into a bone being treated. Optionally, the body can be wholly or partially expanded before the coating is performed. Optionally, the coated body can be dried with air or by other means when the applied formulation is wet, such as a liquid or a gel. The body is refolded as required and either used immediately or stored, if appropriate and desired. Coated on the body, therapeutic substances can be delivered while cancellous bone is being compressed, or with an additional body once the cavity is made.

The methods described above can also be used to coat Gelfoam or other agents onto the body before use. Inflating the Gelfoam-coated body inside bone will further fill any cracks in fractured bone not already filled by the compressed cancellous bone.

Figure 42C:
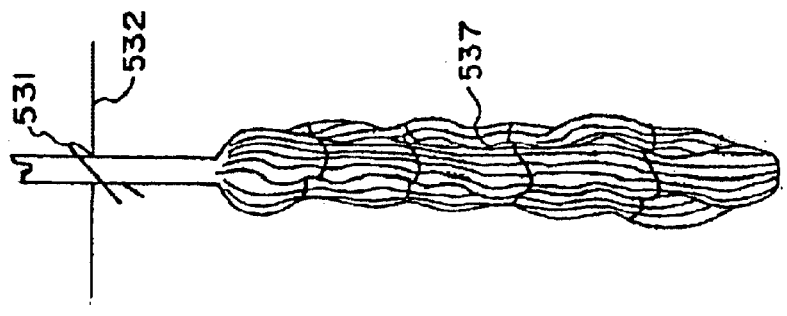
FIGS. 42A to 42C are schematic illustrations of a representative method and system for delivering a therapeutic substance to a bone using an expandable body.
Figure 42B:
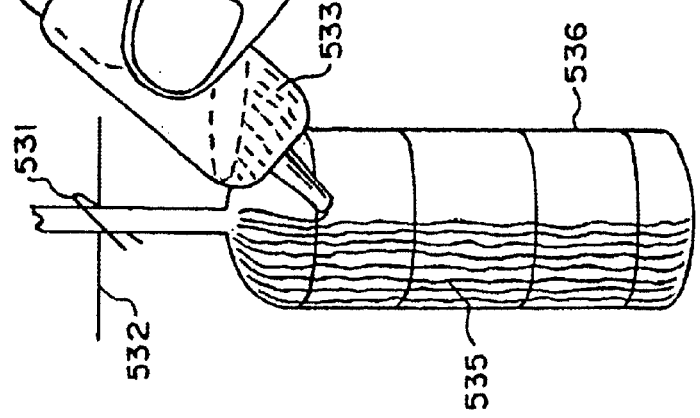
Figure 42A:
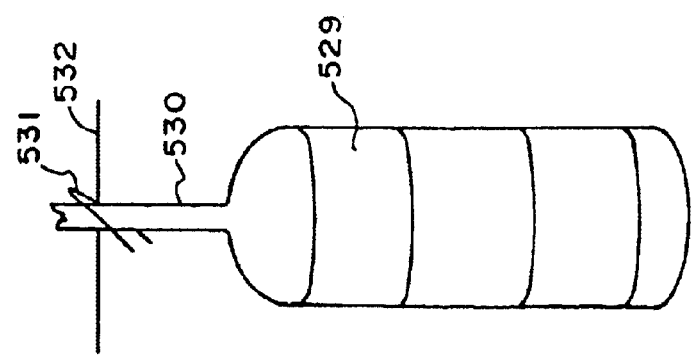

FIGS. 42A to 42C schematically illustrate one system and method for delivering a therapeutic substance to the bone using an expandable body 529. The body 529 is carried at the end of the catheter tube 530, which conveys liquid to expand the body 529, as previously described.

As shown in FIG. 42A, the expandable body 529, in a substantially expanded condition, is stabilized with a clip 531 that couples the catheter tube 530 to a wire 532. As shown in FIG. 42B, a measured amount of gel formulation containing the desired amount of substance 533 is uniformly dispensed from a container 534, preferably in thin lines 535, onto the outer surface of the body 536. The coating substance can be the desired compound alone in its natural state (solid, liquid or gas) or in an appropriate formulation, including a dry powder, an aerosol or a solution. As shown in FIG. 42C, the coated body 537 is collapsed and allowed to dry until the gel sets. Alternatively, the body 536 can also be coated without prior expansion. The optional drying time will, of course, depend on the nature of the compound and its formulation. The coated body 237 is suitable for packaging for use by a surgeon.

Delivering a therapeutic substance on the outside of expandable body used to compact the bone, or with an expandable body introduced after the bone is compacted, is qualitatively different than putting formulated drug into the cavity. When delivered while the bone is compressed, the therapeutic substance becomes incorporated into the compacted bone. This can serve as a way to instantly formulate a slow release version of the substance.

The cavity formed by the expandable body can be filled with an appropriate supporting material, like acrylic bone cement or biocompatible bone substitute, as before described.

Medically-effective amounts of therapeutic substances are defined by their manufacturers or sponsors and are generally in the range of 10 nanograms to 50 milligrams per site, although more or less may be required in a specific case.

For example, the cavity can accommodate a typical dose of the antibiotic, gentamicin, to treat a local osteomyelitis (bone infection). A typical dose is about 1 gram, although the therapeutic range for gentamicin is far greater, from 1 nanogram to 100 grams, depending on the condition being treated and the size of the area to be covered. A medically-suitable gel formulated with appropriate gel materials, such as Polyethylene glycol, can contain 1 gram of gentamicin in a set volume of gel, such as 10 cc.

Other antibiotics that can be used to treat bone infection include, for example, ancef, nafcillin, erythromycin, tobramycin, and gentamicin. Typical bone growth factors are members of the Bone Morphogenetic Factor, Osteogenic Protein, Fibroblast Growth Factor, Insulin-Like Growth Factor and Transforming Growth Factor alpha and beta families. Chemotherapeutic and related agents include compounds such as cisolatin, doxcrubicin, daunorubicin, methotrexate, taxol and tamoxifen. Osteoporosis drugs include estrogen, calcitonin, diphosphonates, and parathyroid hormone antagonists.

VI. Delivery of Biomaterials

A cavity created in cancellous bone by any of the expandable bodies described above can also be filled with biomaterials.

Biomaterials which do not flow into the formed cavity, like hydroxyapatite granules or bone mineral matrix, can be pushed down a tube with a long pin whose diameter is slightly more narrow than the inner-diameter of the outer guide sheath, using the minimally-invasive procedure. During open surgery, the physician can approach the bone in the same way.

If the biomaterial to be inserted does not flow and should not be pushed into the cavity through the guide sheath (as in the case of the hydroxyapatite block, because that can cause damage), the physician can form the cavity using a minimally invasive approach, then punch a hole using standard tools (such as a punch, gouge or rasp) into one side of the cortical bone to allow insertion of the block.

VII. Bone Marrow Harvesting

Any of the expandable bodies described above can also be used in the harvesting of bone marrow for diagnostic or therapeutic purposes, for example, in the diagnosis of multiple myeloma or in the treatment of advanced cancers with bone marrow transplants.

Figure 47:
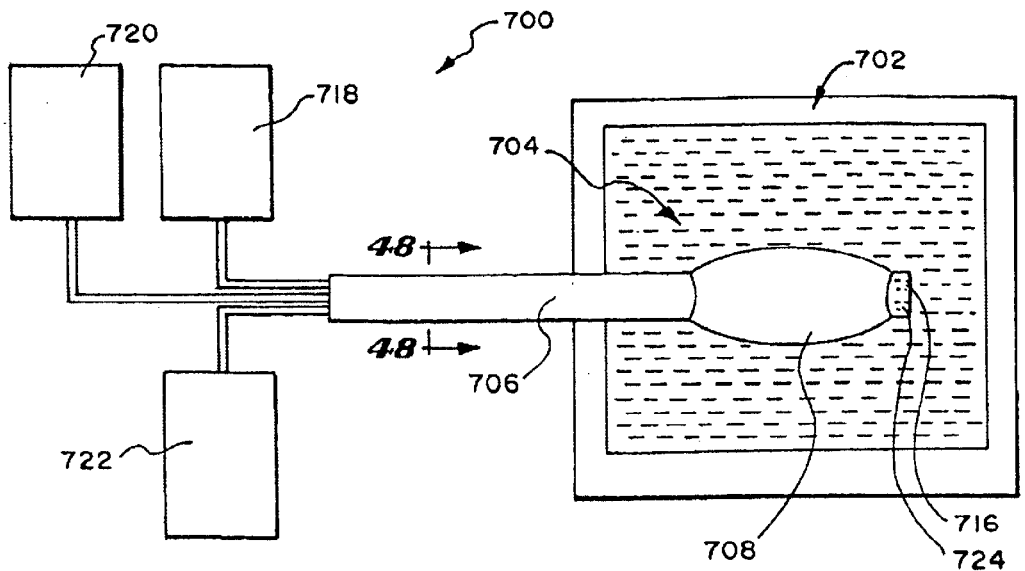
FIG. 47 is diagrammatic view of a system for harvesting bone marrow in a bone-marrow producing bone using an expandable body.

FIG. 47 shows a system 700 for harvesting bone marrow in a bone-marrow producing bone 702. The bone 702, which is shown diagrammatically in FIG. 47, can comprise, for example, the pelvis, or a vertebral body, or a distal radius.

The system 700 employs a bone marrow harvesting tool 704. The tool 704 includes a catheter tube 706, which carries an expandable body 708 at its distal end. The tool 704 can be deployed into the bone 702 using a minimally invasive approach, as previously described.

Figure 48:
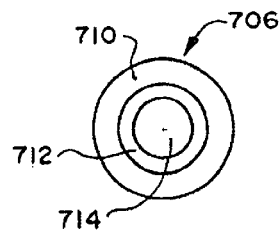
FIG. 48 is a section view of the catheter tube associated with the system shown in FIG. 48, taken generally along line 48—48 of FIG. 47.
Figure 49:
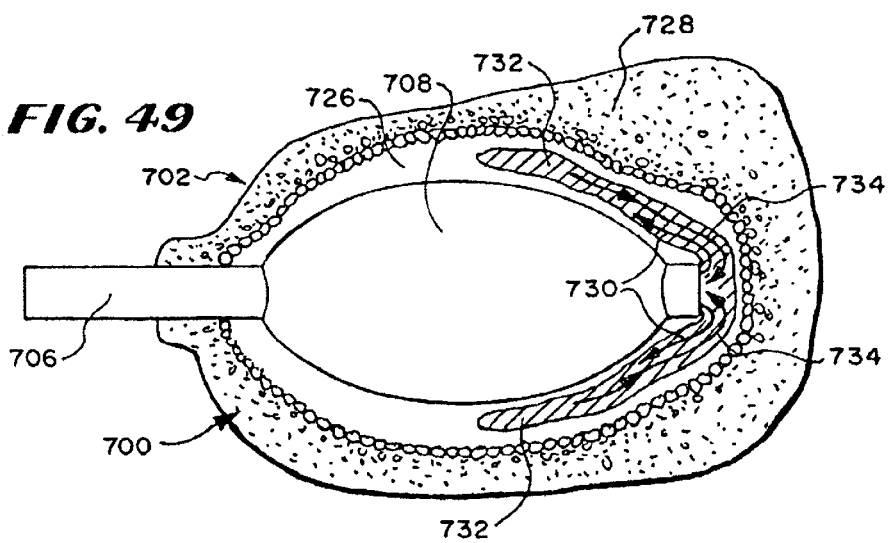
FIG. 49 is an enlarged view of the expandable body associated with the system shown in FIG. 47 inside a bone for the purpose of harvesting bone marrow.

The catheter tube 706 has three concentric and independent lumens 710, 712, and 714 (see FIG. 48). The outer lumen 710 communicates with the interior of the body 78 and is coupled to a source 718 of an inflation liquid. The middle lumen 712 communicates with a source 720 of rinse liquid and a distal opening 716 on the catheter tube 706. The center lumen 714 communicates with a collection container 722 and a second distal opening 724 on the catheter tube 706.

The body 708 is deployed in a substantially collapsed condition, as already described. Inflation liquid, which is preferably radiopaque, is convey from the source 718 into the body 708 to expand it.

As FIG. 48 shows, the body 708 is constrained by selection of relatively inelastic materials or by exterior restraints (as previously described) to assume an elongated shape. Expansion of the body 708 creates a relatively shallow area of compaction 726 in cancellous bone 728 along a relatively long length. The size and shape of the body 708 will depend upon the geometry of the harvest site and the amount of bone marrow required. In long bones, like the distal radius, and in bones with narrow width but large area, such as the ribs or pelvis, the body 728 is shaped to compress a large area but not a great depth of cancellous bone 728.

As FIG. 48 also shows, as the body 708 expands, rinse liquid, which can be saline or another suitable biocompatible liquid, is conveyed from the source 720 into the area 726 (shown by arrows 730 in FIG. 48). The rinse liquid loosens up biological components (such as red blood cells, bone cells, and immune-β cells) within the defined area 726, forming component-rich suspension 732.

The body 708 is collapsed, and suction is applied through the lumen 714. The suction draws the component-rich suspension 732 from the area 726 into the collection container 722.

The above sequence of expansion, rinsing, collapse, and aspiration can be repeated to collect additional component-rich suspension 732 in the container 722. The position of the expandable body 708 in the bone 702 can be changed, if desired, to maintain a component-rich suspension 732 for harvesting.

Use of the expandable body 708 to form the long but shallow compaction area 726 permits the harvest of a significant concentration of therapeutic biological components with less damage to bone that conventional harvesting methods. If desired, standard casts or other fixation devices can be applied to the bone 702 after bone marrow harvesting until the bone 702 heals.

The features of the invention are set forth in the following claims.

We claim:

1. A system for treating a vertebral body having an interior volume occupied, at least in part, by cancellous bone comprising a first tool sized and configured to be introduced into the vertebral body through a percutaneous access path and including an expandable region sized and configured to form a void in the cancellous bone, and a second tool sized and configured to be introduced into the vertebral body through a percutaneous access path and including a platform region sized and configured to be disposed relative to the expandable region of the first tool to define an expansion barrier that directs expansion of the expandable region away from the platform region to direct expansion of the expandable region in a desired direction.

2. A system as in claim 1 wherein the expandable region of the first tools is sized and configured to compact cancellous bone.

3. A system as in claim 1 wherein expansion of the expandable region of the first tool exerts force upon cortical bone.

4. A system as in claim 1 wherein expansion of the expandable region of the first tool exerts force upon cortical bone to move fractured cortical bone.

5. A system as in claim 1 wherein the expandable region of the first tool and the platform region of the second tool comprise parts of a single device.

6. A system as in claim 1 wherein the expandable region of the first tool and the platform region of the second tool comprise separate structures.

7. A method for treating a vertebral body having an interior volume occupied, at least in part, by cancellous bone comprising providing a system as defined in claim 1, introducing the first and second tools into the certebral body, and forming a void in the cancellous bone by expanding the expandable region of the first tool with the platform region of the second tool disposed to serve as an expandable barrier that directs expansion of the expandable region away from the platform region.

8. A method as in claim 7 wherein expanding the expandable region compacts cancellous bone.

9. A method as in claim 7 wherein expanding the expandable region exerts force upon cortical bone.

10. A method as in claim 7 wherein expanding the expandable region exerts force upon cortical bone to move fractured cortical bone.

11. A system for treating a vertebral body having an interior volume occupied, at least in part, by cancellous bone comprising a first tool sized and configured to be introduced into the vertebral body through a percutaneous access path and including a void forming region that enlarges to form a void in the cancellous bone, and a second tool sized and configured to be introduced into the vertebral body through a percutaneous access path and including a platform region sized and configured to be disposed relative to the void forming region of the first tool to define a barrier that directs enlargement of the void forming region away from the platform region to in a desired direction to form the void.

12. A system as in claim 11 wherein the void forming region of the first tool is sized and configured to compact cancellous bone.

13. A system as in claim 11 wherein enlargement of the void forming region of the first tool exerts force upon cortical bone.

14. A system as in claim 11 wherein enlargement of the void forming region of the first tool exerts force upon cortical bone to move fractured cortical bone.

15. A system as in claim 11 wherein the void forming region of the first tool and the platform region of the second tool comprise parts of a single device.

16. A system as in claim 11 wherein the void forming region of the first tool and the platform region of the second tool comprise separate structures.

17. A method for treating a vertebral body having an interior volume occupied, at least in part, by cancellous bone comprising providing a system as defined in claim 11, introducing the first and second tools into the vertebral body, and forming a void in the cancellous bone by enlarging the void forming region of the first tool with the platform region of the second tool disposed to serve as a barrier that directs enlargement of the void forming region away from the platform region.

18. A method as in claim 17 wherein enlarging the void forming region compacts cancellous bone.

19. A method as in claim 17 wherein enlarging the void forming region exerts force upon cortical bone.

20. A method as in claim 17 wherein enlarging the void forming region exerts force upon cortical bone to move fractured cortical bone.

21. A system for treating a vertebral body having an interior volume occupied, at least in part, by cancellous bone comprising
a first tool sized and configured to be introduced into the vertebral body through a percutaneous access path and including a compacting region that enlarges to form a void in the cancellous bone and compact the cancellous bone, and
a second tool sized and configured to be introduced into the vertebral body through a percutaneous access path and including a platform region sized and configured to be disposed relative to the compacting region of the first tool to define a barrier that directs enlargement of the compacting region away from the platform region in a desired direction to form the void and compact the cancellous bone.

22. A system as in claim 1 or 11 or 21 wherein the platform region comprises an expandable body.

23. A system as in claim 22 wherein the expandable body is inflatable.

24. A system as in claim 22 wherein the expandable body is a balloon.

25. A system as in claim 22 wherein the expandable body has a predetermined shape and size when expanded.

26. A system as in claim 1 or 11 or 21 wherein at least one of the first and second tools includes an elongated shaft sized and configured to pass through a percutaneous access path.

27. A system as in claim 26 wherein the elongated shaft comprises a catheter.

28. A system as in claim 21 wherein enlargement of the compacting region of the first tool exerts force upon cortical bone.

29. A system as in claim 21 wherein enlargement of the compacting region of the first tool exerts force upon cortical bone to move fractured cortical bone.

30. A system as in claim 21 wherein the compacting region of the first tool and the platform region of the second tool comprise parts of a single device.

31. A system as in claim 21 wherein the compacting region of the first tool and the platform region of the second tool comprise separate structures.

32. A method for treating a vertebral body having an interior volume occupied, at least in part, by cancellous bone comprising
providing a system as defined in claim 21,
introducing the first and second tools into the vertebral body, and
forming a void in the cancellous bone and compacting the cancellous bone by enlarging the compacting region of the first tool with the platform region of the second tool disposed to serve as a barrier that directs enlargement of the compacting region a way from the platform region.

33. A method as in claim 32 wherein enlarging the compacting region exerts force upon cortical bone.

34. A method as in claim 32 wherein enlarging the compacting region exerts force upon cortical bone to move fractured cortical bone.

* * * * *

UNITED STATES PATENT AND TRADEMARK OFFICE
CERTIFICATE OF CORRECTION

PATENT NO. : 6,899,719 B2
DATED : May 31, 2005
INVENTOR(S) : Mark A. Reiley et al.

It is certified that error appears in the above-identified patent and that said Letters Patent is hereby corrected as shown below:

Column 27,
Line 49, after "first" delete "tools" and substitute -- tool --.

Column 28,
Line 2, after "into the" delete "certebral" and substitute -- vertebral --.
Line 31, before "in" delete "to".

Column 30,
Line 28, after "region" delete "a way" and substitute -- away --.

Signed and Sealed this

Twenty-third Day of August, 2005

JON W. DUDAS
*Director of the United States Patent and Trademark Office*